(12) United States Patent
    Mills

(10) Patent No.: US 10,709,375 B2
(45) Date of Patent: Jul. 14, 2020

(54) DEVICES, SYSTEMS AND METHODS FOR TESTING FOR DEGENERATIVE DISORDERS OF THE CENTRAL NERVOUS SYSTEM

(71) Applicant: Inspired Technologies, Inc., LeSueur, MN (US)

(72) Inventor: Gregory B. Mills, Kansas City, KS (US)

(73) Assignee: Inspired Life Medical, Inc., LeSueur, MN (US)

( * ) Notice: Subject to any disclaimer, the term of this patent is extended or adjusted under 35 U.S.C. 154(b) by 198 days.

(21) Appl. No.: 16/031,230

(22) Filed: Jul. 10, 2018

(65) Prior Publication Data

US 2020/0015733 A1    Jan. 16, 2020

(51) Int. Cl.
    *A61B 5/00*        (2006.01)
    *A61B 5/087*       (2006.01)
(52) U.S. Cl.
    CPC .......... *A61B 5/4011* (2013.01); *A61B 5/0002* (2013.01); *A61B 5/0873* (2013.01); *A61B 5/0875* (2013.01)
(58) Field of Classification Search
    CPC ... A61B 5/4011; A61B 5/0002; A61B 5/0873; A61B 5/0875
    See application file for complete search history.

(56) References Cited

U.S. PATENT DOCUMENTS

| | | | |
|---|---|---|---|
| 6,558,322 | B1 | 5/2003 | Busch |
| 6,644,305 | B2 | 11/2003 | MacRae et al. |
| 6,713,024 | B1 | 3/2004 | Arnell et al. |
| 7,740,014 | B2 | 6/2010 | Djupesland |
| 9,021,860 | B2 | 5/2015 | Nelson |
| 2013/0312749 | A1 | 11/2013 | Bornn et al. |
| 2015/0112161 | A1* | 4/2015 | Mills ....................... A61B 5/742 600/303 |
| 2016/0015309 | A1* | 1/2016 | Mills .................... A61B 5/4088 600/303 |

(Continued)

OTHER PUBLICATIONS

Lorig et al., "A computer-controlled olfactometer for fMRI and electrophysiological studies of olfaction," Behavior Research Methods, Instruments, & Computers vol. 31, pp. 370-375(1999) (Year: 1999).*

(Continued)

*Primary Examiner* — Eric J Messersmith
(74) *Attorney, Agent, or Firm* — Barnes & Thornburg LLP; Jeffrey R. Stone

(57) ABSTRACT

The present system is directed in various embodiments to devices, systems and methods for detection, evaluation and/or monitoring olfactory dysfunction by measuring and determining the patient's olfactory detection threshold for the left and the right nostril. In some cases, the present invention relates to devices, systems and methods for detecting an asymmetric differential in a patient's relative olfactory detection and/or identification threshold (left vs right nostril) which, when present, may be used as a device to detect, diagnose and/or monitor olfactory deterioration resulting from Alzheimer's disease, and/or the efficacy of treatment regimens therefor over time. Alternatively, general olfactory dysfunction may be evaluated and/or monitored without regard to the individual nostril's performance.

20 Claims, 11 Drawing Sheets

(56) References Cited

U.S. PATENT DOCUMENTS

| | | |
|---|---|---|
| 2016/0095544 A1 | 4/2016 | Martino |
| 2017/0097340 A1 | 4/2017 | Ho et al. |
| 2017/0258387 A1 | 9/2017 | Mills |
| 2018/0110457 A1 | 4/2018 | Smith et al. |

OTHER PUBLICATIONS

Stamp et al. "A Brief Olfactory Test for Alzheimer's Disease", 2 pages. J Neurol Sci. Oct. 15, 2013; 333(0).

International Search Report and Written Opinion issued in related PCT application No. PCT/US2019/040907, dated Oct. 1, 2019.

* cited by examiner airways further apart airways closer

DEVICES, SYSTEMS AND METHODS FOR TESTING FOR DEGENERATIVE DISORDERS OF THE CENTRAL NERVOUS SYSTEM

FIELD OF THE INVENTION

The present invention generally relates to devices, systems and methods for testing, screening and/or diagnosing degenerative disorders of the central nervous system. More specifically, the present invention relates to devices, systems and methods for detecting symmetric or an asymmetrical differential in a patient's olfactory detection threshold as measured at the left and right nostrils.

DESCRIPTION OF THE RELATED ART

Testing a person's ability to recognize certain odors is well known and used in a variety of contexts, including employment screening for jobs requiring a baseline threshold ability to smell certain chemicals, etc. Certain diseases and/or conditions are known to cause a decrease in the ability to smell odors. For example, various neurological conditions, including for example brain injury may result in a reduced ability to smell some or all odors. In addition, central nervous system disorders, e.g., Parkinson's disease and general neurodegeneration also are known to result in a general reduced olfactory capability across both the left and right nostrils, while Alzheimer's disease is known to begin with left olfactory lobe deterioration leading to an initial loss of olfactory capability for certain odors presented to the left nostril compared with the right.

A notable deficit of smelling ability in the left nostril as compared to the smelling ability of the right nostril to detect a pure aroma or pure odorant (as defined further herein), appears according to previous medical research, to be indicative of early neurological degeneration of the olfactory nerve, specifically as seen in the early onset of AD.

Applicant has developed several solutions for improved diagnostic methods related to bilateral and lateral olfactory screening as further described in the following references, all assigned to current applicant Inspired Technologies, the entire contents of each of which are hereby incorporated by reference:

U.S. Pat. No. 9,717,454 entitled "Method of Ruling Out Alzheimer's Disease";

U.S. Pat. No. 9,801,581 entitled "Devices, Systems and Methods for Detecting a Bilateral Differential in Olfactory Threshold for Pure Odorants";

U.S. Pat. No. 9,936,913 entitled "Methods for Cascading Pure Odorants to the Nostrils of Patients";

US Publication 20160249844 entitled "Method for Screening a Patient for Alzheimer's Disease"; and US Publication 20170258387 entitled "Devices, Systems and Methods for Screening for Alzheimer's Disease by Detecting a Differential in Olfactory Identification for Pure Odorants.

The "relative olfactory sensitivity" of the two nostrils (right and left) is a preferred biometric differential being sought for lateral and/or bilateral olfactory damage assessment, rather than "absolute sensitivity" using embodiments of the present invention, though absolute sensitivity testing for each nostril is within the scope of the present invention.

Some people have been exposed to industrial chemicals or noxious paint fumes, e.g., that have damaged their sense of smell. However such chemicals likely impacted both nostrils relatively equally since such damaging chemical exposure was equal. In addition, research indicates that a relative equal loss of the sense of smell for pure aromas on both sides, as compared to a normal detection level, might be indicative of other neurological diseases, such as Parkinson's disease which impacts both nostrils equally.

Surgery or a serious brain infection or serious head trauma for example, might render one nostril's sensitivity damaged or completely unable to function without presenting an accurate indication of AD linked olfactory damage.

Generally however, a deteriorated sense of pure aroma or odorant detection in the left nostril greater than the right nostril is neurologically significant when the subject is screened. Such pure aroma screens indirectly assess the condition of the olfactory nerve by presenting pure aroma in a controlled way, such that the concentration and sort of aroma is manipulated by the testing personnel and only one nostril at a time is served aroma. The relative differential in strength of the nostrils, tested one nostril at a time, is the underlying biometric of interest in more efficaciously detecting AD than testing both nostrils at once.

Thus, a need exists in the art generally for an inexpensive, easy to use, accurate and repeatable clinically significant device, system and method for detecting an asymmetric (left vs right) differential in the olfactory detection threshold of a patient. Such devices, systems and methods may be used to assist a physician in screening and/or detecting incipient AD, in many cases before the clinical presentation of dementia occurs.

In addition to the above asymmetrical (left vs right) olfactory threshold discussion, certain disorders or conditions may result in a symmetric, or general, olfactory threshold deterioration which may be used to monitor the progression of the underlying disorder or condition and/or the efficacy of a treatment plan designed for the disorder or condition.

A partial listing of conditions or disorders that comprise olfactory dysfunction that may result in either symmetric or asymmetric olfactory threshold deterioration and, therefore, amenable to detection, evaluation and/or monitoring using embodiments of the present invention discussed herein, follows:

Endocrine Conditions or Disorders
  Adrenal cortical insufficiency;
  Cushing's syndrome;
  Diabetes mellitus;
  Hypothyroidism;
  Kallman's syndrome;
  Primary amenorrhea;
  Pseudohypoparathyroidism; and
  Turner's syndrome.
Neurodegenerative and/or Central Nervous System Conditions or Diseases
  Alzheimer's disease;
  Parkinson's disease;
  Huntington's disease;
  Mild cognitive impairment;
  Dementia;
  Multiple sclerosis;
  Epilepsy;
  Traumatic brain injury (TBI);
  Concussion; and
  Intracranial surgery.
Nutritional Conditions and/or Disorders
  Vitamin B12 deficiency (cyanocobalamin);
  Renal failure; and
  Korsakoff's psychosis.
Psychiatric Conditions and/or Disorders Depression;
Olfactory reference syndrome;
Seasonal affective disorder; and
Schizophrenia.
Local Diseases and/or Mechanical Obstruction of Airway
Adenoid hypertrophy;
Allergic rhinitis;
Atrophic rhinitis (ozena);
Bronchial asthma;
Exposure to toxic chemicals;
Leprosy;
Malignant of paranasal sinuses;
Nasal polyposis;
Sinusitis;
Sjogren's syndrome; and
Vasomotor rhinitis.
Intranasal Tumors
Frontal lobe glioma;
Hydrocephalus;
Internal carotid aneurysms;
Neuroblastoma;
Suprasellar meningioma;
Sphenoidal ridge meningioma;
Meningioma; and
Aneurisms of the anterior communicating bifurcation.
Viral and Infections Conditions and/or Disorders
Acute viral hepatitis;
Herpes simplex; and
Influenza.

Known general olfactory sensitivity screening methods, e.g., the University of Pennsylvania's "UPSIT" aroma identification device claim to identify general olfactory problems, but do not differentiate between the two nostrils, and therefore fail to identify any odorant threshold differential between the nostrils. These screening methods may be used to screen for general olfactory sensitivity losses, but only if the testing methods and devices are sufficiently optimized and provide accurate, reproducible and therefore useful results.

The UPSIT scratch and sniff scent identification test by design does not differentiate between pure aromas that are perceived exclusively by the first cranial nerve or other non-pure aromas that are perceived by the first and the fifth cranial nerves via the trigeminal system. The man made organic chemical formulations of very well-known pure aromas by name only in the UPSIT are not really pure olfactory specific odorants in practice. The UPSIT 40 or 20 odorants all contain stimulants that trigger a reaction in the trigeminal nerves served by the fifth cranial nerve.

Thus, a need also exists in the art for an inexpensive, non-invasive, easy to use, accurate and repeatable clinically significant device, system and method for detecting, or screening for, a general loss of smell capability, whether the loss is detected via the left and/or right nostril and that may be configured to only stimulate the first cranial nerve.

Further, a need exists in the art for a test comprising a certain concentration of a pure odorant as defined further herein that may be detectable at the left nostril of patient's without Alzheimer's disease, but that is not detectable by patients with damage at the left olfactory bulb as a result of early stage and pre-clinical Alzheimer's disease.

The present invention addresses these, among other, needs.

BRIEF SUMMARY OF THE INVENTION

The present system is directed in various embodiments to devices, systems and methods for detection, evaluation and/or monitoring olfactory dysfunction by measuring and determining the patient's olfactory detection threshold for the left and the right nostril. More specifically, the present invention relates to devices, systems and methods for detecting an asymmetric differential in a patient's relative olfactory detection and/or identification threshold (left vs right nostril) which, when present, may be used as a device to detect, diagnose and/or monitor asymmetric (right vs left) olfactory deterioration resulting from Alzheimer's disease, and/or the efficacy of treatment regimens and/or adjust the treatment regimen over time.

Further, the present system may, in alternate embodiments be used to detect, evaluate and/or monitor general olfactory dysfunction without regard to the individual nostril's performance. In these embodiments, the olfactory detection and/or identification thresholds may be measured and compared with an expected value or score or, alternatively, may be used to establish a baseline for the subject with subsequent testing employed to monitor for deterioration.

DETAILED DESCRIPTION

Figure 1:
FIG. 1 illustrates one embodiment of the present invention.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

The present system is directed in various embodiments to devices, systems and methods for detection, evaluation and/or monitoring olfactory dysfunction by measuring and determining the patient's olfactory detection threshold for the left and the right nostril. More specifically, the present invention relates to devices, systems and methods for detecting an asymmetric differential in a patient's relative olfactory detection and/or identification threshold (left vs right nostril) which, when present, may be used as a device to detect, diagnose and/or monitor olfactory deterioration resulting from Alzheimer's disease, and/or the efficacy of treatment regimens therefor over time.

Further, the present system may, in alternate embodiments be used to detect, evaluate and/or monitor general olfactory dysfunction without regard to the individual nostril's performance. In these embodiments, the olfactory detection and/or identification thresholds may be measured and compared with an expected value or score or, alternatively, may be used to establish a baseline for the subject with subsequent testing employed to monitor for deterioration.

Definitions

As used herein, "symmetric" or "symmetrical" means that there is not a significant differential in the subject patient's ability to detect and/or identify odors between odors administered and/or inhaled into the patient's left nostril vs. the patient's right nostril as measured by the olfactory threshold determined for each nostril.

As used herein, "asymmetric" or "asymmetrical" means that there is a significant asymmetry or differential in the subject patient's ability to detect and/or identify odors between odors administered and/or inhaled into the patient's left nostril vs. the patient's right nostril as measured by the olfactory threshold determined for each nostril.

"Hyperosmia" is defined as increased olfactory acuity, or a decreased threshold for detecting odors, and may be symmetric or asymmetric as those terms are defined herein. Various embodiments of the present invention may detect and/or monitor hyperosmia or treatments therefore.

"Hypoosmia is defined as diminished or decreased olfactory acuity, or an increased threshold for detecting odors, and may be symmetric or asymmetric as those terms are defined herein. Various embodiments of the present invention may detect and/or monitor hypoosmia or treatments therefore.

"Anosmia" is defined as the inability to recognize odors and may be symmetric or asymmetric as those terms are defined herein. Various embodiments of the present invention may detect and/or monitor anosmia or treatments therefore.

"Dysosmia" is defined as the abnormal sense of smell and may be symmetric or asymmetric as those terms are defined herein. Various embodiments of the present invention may detect and/or monitor dysosmia or treatments therefore.

"Olfactory dysfunction" is defined herein as a patient with a disorder and/or condition with one or more of the following: hyperosmia, hypoosmia, anosmia, and dysosmia. The olfactory dysfunction may be symmetric or asymmetric as those terms are defined herein.

"Pure odorant", also referred to equivalently as "pure aroma" is defined as substances including molecules and/or compounds which principally stimulate the olfactory cell receptors associated with the olfactory nerve, aka the first cranial nerve, and that do not trigger or excite the trigeminal nerve associated with the fifth cranial nerve. A non-exhaustive and categorized listing of pure odorants follows:

The pure odorant Spice family comprises:
Cinnamon;
Clove;
Vanilla;
Nutmeg; and
Allspice.

The pure odorant Food family comprises:
Peanut/Peanut Butter;
Coffee;
Cocoa;
Apple;
Almond (bitter); and
Strawberry.

The pure odorant Herbal family comprises:
Peppermint;
Spearmint;
Wintergreen;
Allspice;
Parsley;
Sage;
Turmeric;
Thyme;
Basil;
Dill weed;
Caraway;
Anise;
Fennel;
Mace;
Palmarosa; and
Patchouli.

The pure odorant Floral family comprises:
Rose;
Lemongrass;
Rosemary;
Lavender;
Lilac;
Violet; and
Origanum.

The pure odorant Citrus family comprises:
Orange;
Tangerine;
Lemon;
Lime;
Mandarin;
Grapefruit;
Bergamot and
Petitgrain.

The pure odorant Wood and Resin based family comprises:
Eucalyptus;
Juniper berry;
Pine;
Tea tree;
Spruce;
Ho wood;
Cypress;
Cedar,
Birch;
Fir,
Cajeput;
Camphor;
Cassia;
Citronella;

Clary;
Copaiba;
Elemi;
Hydacheim;
Litsea; and
Niaouli.

Further, the following is a non-exhaustive list of commercially available essential oils that appear to be $1^{st}$ cranial nerve-specific stimulants that, when presented in an effective concentration and without significant contamination with odorants that may stimulate the $5^{th}$ cranial nerve, are unable to substantially stimulate the 5th cranial nerve.

| Listing by Common name, category, botanical name, main organic chemical | |
|---|---|
| Allspice, Spice, *Pimenta dioica* | Eugenol/64.83, Caryophyllene/6.49 |
| Amyris, Wood, *Amyris balsamifera* | |
| Anise Star, Food, *Illicium verum* | |
| Basil, Spice, *Ocimum basilicum* | |
| Bergamot, Wood, *Citrus bergamia* | |
| Birch, Wood, *Betula lenta* | Methyl salicylate/99.44 |
| Black Pepper, Spice, Piper nigrum | Caryophyllene<trans>/27.72, Lemonene/15.20 |
| Cajeput, Wood, *Melaleuca cajuputi* | |
| Camphor, Wood, *Cinnamomum camphora* | |
| Cannabis Sativa (no THC), Herb, *Cannabis sativa* | |
| Caraway, Spice, *Carum carvi* | |
| Carrot Seed, Herb, *Daucus carota* | |
| Cardamom, Flower, *Elettaria cardamomum* | |
| Catnip, Herb, *Nepeta cataria* | |
| Cassia, Wood, *Cinnamomum cassia* | |
| Cedar, Wood, *Cedarus deodora* | |
| Celery Seed, Spice, *Apium graveolens* | |
| Cilantro, Herb, *Coriandrum sativum* | |
| Cinnamon, Spice, *Cinnamomun, cassia* | |
| Citronella, Flower, *Cymbopogon winteriaus* | |
| Clementine, Food, *Citrus clementina* | |
| Clove, Spice, *Syzgium aromaticum* | |
| Cocoa, Food, *Theobroma cacao* | |
| Coffee, Food, *Coffea Arabica* | |
| Copaiba, Wood, *Copaifera officinalis* | |
| Cypress, Wood, *Cupressus sempervirens* | |
| Dill Weed, Spice, *Anethum graveolens* | |
| Elemi, Wood, *Canarium luzonicum* | |
| Eucalyptus, Wood, *Eucalyptus globulus* | |
| Fennel, Grass, *Foeniculum vulgare* | |
| Fir, Wood, *Abies siberica* | |
| Fir Balsam, Wood, *Abies balsamea* | |
| Frankincense, Wood, *Boswellia carterii* | |
| Garlic, Spice, *Allium Sativum* | |
| Galbanum, Flower, *Ferula galbaniflua* | |
| Galangal Root, Flower, *Alpinia galangal* | |
| Ginger Grass Herb, *Cybopogon martini* | |
| Geranium, Flower, *Pelargonium graveolens* | |
| Ginger Grass, Grass, *Zingiber officinale* | |
| Grapefruit, Food, *Citrus paradise* | |
| Hyssop, Bush, *Hyssopus officinalis* | |
| Honeysuckle, flower, Synthetic | |
| Juniper Berry, Bush, *Juniperus commurnis* | |
| Key Lime, food, *Citrus aurantifolia* swingle | |
| Lauyal Leaf, *Laurus nobilis* | |
| Lavender, Flower, *Lavandula officinalis* | |
| Lemongrass, Grass, *Cymbopogon flexuosus* | |
| Lemon, Food, *Citrus limon* | |
| Lime, Food, *Citrus aurantifolia* | |
| Litsea, Wood, *Litsea cubeba* | |
| Muhuhu, Wood, *Brachyleana hutchinsii* | |
| Myrrh, Wood, *Commiphora myrrha* Furanocudesma-1,3-diene/31.28; Curzerene 29.11 | |
| Myrtle, Tree, *Myrtus communis* | |
| Niaouli, Wood, *Melaleuca quinquenervia* | |
| Nutmeg, Spice, *Myristica fragrans* | b-pinene/sabinene/38, a-pinene/16 |
| Mandrarin Orange Food, *Citrus reticula* | |
| Opoponax, Wood, *Commiphora erythraea* | |
| Oregano, Spice, *Origanum vulgare* | |
| Palmarosa, tree *Cymbopogon martini* | |
| Pomegranate, Food, *Punica granatum* | |
| Palo Santo, Wood, *Bursera graveolens* | Limonene/68, Terpineol/10, menthofuran/10 |
| Plai, Wood, *Zingiber cassumunar* | |
| Patchouli, Wood, *Pogostemon cablin* | |
| PennyRoyal, Flower, *Mentha pulegium* | |
| Petitgrain, Wood, *Citrus aurantium* | |
| Peppermint, Food, *Mentha piperata* | |
| Pine, Wood, *Pinus pinaster* | |
| Pimento, Food, *Pimenta officinalls* | |

| Listing by Common name, category, botanical name, main organic chemical |
| --- |
| Ravensara, Wood, *Ravensara aromatic* |
| Ravensara Cinnamon, Spice, *Cinnamomum camphora* |
| Rose, Flower, Rosaceae |
| Rosemary, Flower, *Rosemarinus officinalis* |
| Camphor/38, a-pinene/35, Myrcene/18 |
| Rosewood, Wood, *Aniba rosaeodora* |
| Sage, Bush, *Salvia officinalis* |
| Spike Lavender, *Lavandula latifolia* |
| Spikenard, Flower, *Nardostachys jatamansi* |
| Spruce, Wood, *Picea mariana* |
| Spearmint, Food, *Mentha spicata* |
| Sweet Orange, *Citrus Sinensis* |
| Tangerine, Food, *Citrus reticuata* |
| Tea, Food, *Melaleuuca alternifolia*    Terpinolene-4-OL-41/Gama-Terpinene/20, Alpha-Terpinene/9 |
| Turmeric, Bush, *Curcuma longa* |
| Thyme, Spice, *Thymus zygis* |
| Vanilla, Food, *Vanilla planifolia* |
| Violet, Flower, *Viola odorata* |
| Verbena, Wood, *Lippia javanica* |
| Watermelon, Food, *Cirullus lanatus* |
| Wild Orange, food, *Citrus sinensis* |
| Wormwood, Wood, *Artemisia absinthium* |
| Wintergreen, Food, *Gaultheria procumbens* |
| Ylang Ylang, Flower, *Canaga odorata* |

"Effective amount" of the odorant or pure odorant is defined as the minimum amount of pure odorant required to infuse the aroma airway passage during operation of the various devices, systems and methods of the present invention sufficiently to enable a patient to smell the pure odorant, i.e., when saturation of the olfactory nerve is sufficient to enable the reaching of the pure odorant detection threshold for the patient and nostril being tested.

Dilution, serial, stepped or otherwise, with water, fractionated coconut oil or other suitable diluent for certain aromas that are proportionally much stronger than others might make them more useful for testing purposes, including but not limited to identification testing. For example, lemon essential oil is perceived as having a particularly strong aroma which might need to be diluted more than most to not stand out so much based only upon its inherent aroma strength. Careful dilution also creates sets of increasing concentrations that are useful for testing to determine a minimum concentration that is detectable by each nostril.

"Pure odorant detection threshold" is defined as the point at which the concentration of pure odorant molecules saturate the olfactory nerve to the extent that a cognitive reaction first takes place. At this point, the subject patient is able to express that he or she is smelling something, but not necessarily able yet to identify the aroma by name. The pure odorant detection threshold may be found to be asymmetrical, i.e., significantly different as between the nostrils, indicating olfactory dysfunction. Alternatively, the pure odorant detection threshold may be found to be symmetrical between the tested nostrils and may be considered normal or may be determined to comprise a general loss of olfactory capability that is substantially equal between the nostrils, and olfactory lobes. This latter case may be indicative of, inter alia, a general olfactory problem.

"Pure odorant identification threshold" may represent a slightly longer latent period than the "pure odorant detection threshold" as it is defined as the point at which the patient is able to actually identify, or attempt to identify, the pure odorant by name or alternate identifier, indicating that cognitive processing has occurred. The pure odorant identification threshold may be found to be asymmetrical, i.e., significantly different as between the nostrils, indicating lateral olfactory dysfunction. Alternatively, the pure odorant identification threshold may be found to be symmetrical between the tested nostrils and may be considered normal or may be determined to comprise a general loss of olfactory capability that is substantially equal between the nostrils, and olfactory lobes.

"Pure Odorant" is defined herein as a compound that does not substantially stimulate or trigger the $5^{th}$ cranial nerve.

"Odorant detection threshold" is defined as the point at which the concentration of odorant molecules saturate the olfactory nerve to the extent that a cognitive reaction first takes place. At this point, the subject patient is able to express that he or she is smelling something, without necessarily identifying the aroma. The odorant detection threshold may be found to be asymmetrical, i.e., significantly different as between the nostrils, indicating olfactory dysfunction. Alternatively, the odorant detection threshold may be found to be symmetrical between the tested nostrils. In either case, one or more of the tested nostrils/sides (left vs right) may be determined to have an olfactory capability deficit, either compared to a population standard, or to a baseline established by and for the subject.

"Odorant identification threshold" is defined herein as the point at which the patient is able to actually identify the odorant by name or alternate identifier, indicating that cognitive processing has occurred. The odorant identification threshold may or may not be symmetrical between the nostrils.

"Alternative identifier" is defined as something other than a common name or scientific name of an aroma that identifies or distinguishes an odorant. Exemplary alternative identifiers, may comprise category such as a flower, a wood, a spice, a food. Situations where the odorant may be smelled might be at breakfast, at dinner, at a doctor's office. A place where such an aroma may be commonly be smelled might be a restaurant, a lumber yard, a flower bed. An identifier might be identified as the odorant before or after, a new odorant, an odorant that was presented previously or not presented or a stronger or weaker odorant.

"Clear air", also referred to as pure air, is defined as air that does not comprise the odorant used in the inventive embodiments of the present invention. Preferably, clear air comprises air that is substantially uncontaminated by any odorant, including pure odorants. Clear air may comprise ambient air, i.e., atmospheric air, either filtered or unfiltered, or air that is provided from a clear air source such as an air tank or nebulizer and/or from a mechanized powered air pump as is well known in the art.

"Reset Period" is defined as a rest time between presentations or introductions of odorants or pure odorants, known reset periods are in the range of 90 seconds.

Aroma detection testing is done for many reasons and in a number of ways to accomplish various purposes, including diagnostic medical tests. Odor identification for example, comprise a common olfactory function that is tested. Known odor identification devices and methods have been developed to screen for what might be called a "scent memory function". This sort of testing metric might be referred to as "Tell me what you smell?" and measured in one or more of: the correct response, any response whether or not correct, the time, e.g., seconds, to reach the response, or the number of breaths or inhalations required to reach the response. These metrics thus correspond to the presently defined "pure odorant identification threshold".

Pure aroma olfactory detection threshold response time is also of particular clinical interest, especially when done bilaterally. In other words, the same aroma sensing test is preformed separately on each nostril and the test results compared, left nostril vs right nostril. This is done without aroma identification even being required. Perhaps the metric could be referred to as "Tell me when you smell something" and may be measured in one or more of: the reaching of a responsive point and communication of same, the time, e.g., seconds, to reach the responsive point, or the number of breaths or inhalations required to reach the response. These metrics correspond to the "pure odorant detection threshold" as defined herein.

Concentrations of a single aroma, whether odorant or pure odorant, may be gradually increased, in even or other incremental steps, presented to the nostril until cognitive awareness of the presence of the aroma is noted. Alternatively, one or more aromas may be presented, each with one or more concentrations.

The Alcohol Sniff Test for general smelling awareness is well known, where an alcohol wipe is opened, the patient's eyes closed as they attempt to smell the alcohol as the odorant is slowly moved closer to the nostrils as measured by a ruler. Theoretically, someone who can't smell the alcohol wipe until it very close has a weaker sense of smell as someone who can smell it further away. The ruler provides a numerical scale used as data.

Several aroma testing researcher have adapted the Alcohol Sniff Test concept to detect the lateral ability of the nostrils by having the patient cover the other nostril while testing the open nostril. The distance to the aroma testing method can specifically screen for olfactory sensitivity rather than trigeminal sensitivity by using any known olfactory specific pure odorant. However, covering one nostril may lead to exaggerated ill-regular breathing through the open nostril and potentially skew the data. Breathing a plurality of ever stronger concentrations of aroma each breath tends to cumulatively saturate the olfactory nerves without allowing cleansing breaths between smelling aroma samples.

The concentrations levels of aroma vary dramatically within an open plume of odorant in air. Concentrations tend, according to Boyle's law, to dissipate in the atmosphere logarithmically, from the strongest concentrations found at the center of the plume to the weaker outer edges of the plume. Obviously, measuring concentrations of aroma that dissipate on a logarithmic scale with a liner scale is poor science and can lead to serious distortions in the data.

An uncontrolled open plume of aroma is also subject to being blown around by the test subject and testing personnel breathing, making measuring exactly how far the plume was from the nostril at the point of detection impossible to determine.

A plurality of evenly, or other, stepped samples of increasing concentration of an olfactory specific odorants may be channeled to one nostril at a time to overcome the open plume problems stated above. Evenly increased concentrations of an aroma in small equal steps can be expressed correctly as linear concentrations, overcoming the logarithmic progression of an open plume.

Providing channeled aroma samples to one nostril while bypass clean air is channeled to the other nostril avoids air hunger and distorted breathing through one nostril since normal bilateral air supply is maintained.

Channeling aroma to the nostril being tested prevents an uncontrolled plume of aroma being blown around potentially distorting the diagnostic results.

Presenting single aroma samples one at a time allows cleansing breaths between each test sample to reduce cumulatively saturating the olfactory nerves before the actual detectable sample is presented.

Numbering or marking with a code, each sample a plurality of aromas from lowest to highest concentration allows the indica of the aroma sample detected to be the data.

Using a set of aromas sequentially, first for one nostril and then the other nostril provides a differential that compares the results of the two nostril that is more scientifically repeatable.

Stopping the presentation of a plurality of ever increasing concentrations of aromas as soon the nostril being tested detect it, reduces aroma fatigue and potential aroma latency issues.

Alternatively, the time interval can be measured in seconds between aroma presentation to the subject, who is inhaling through an aroma presentation device, until the time interval ends upon cognitive notice that an aroma was noted. "Tell me the second you smell the aroma". Time in seconds may be the metric recorded, indirectly measuring the level of odor concentration of aroma required to trigger cognitive notice.

Aroma identification as a testing method can be achieved by offering multiple choice selection where right vs wrong aroma names are the multiple choice selections.

Identification as a metric of scent testing can also be multiple choice of the aromas presented, select the event or place where the aroma may normally be smelled. The aroma "coffee" may be smelled at A. cafe, B. lumber yard, C. flowerbed, D. forest, E. church.

Similarly, the number of breaths taken, and/or the time in e.g., seconds, from the point of first introduction or presentation of the aroma until cognitive notice by the subject is a valid metric indirectly scaling the aroma detection ability of the nostrils and can make the data set more robust.

The metric of a single aroma might be considered comparing no smell in the air as a baseline compared to a slowly increasing, evenly or unevenly stepped, concentration of pure aroma infused in clear room and recording some definable metric used for clinical comparison between the nostrils. All of these metrics indirectly score olfactory function for detection of pure aromas.

Detection of one aroma in stepped increasing concentrations can be offered sequentially, with the instruction to the subject "when you first detect the rose aroma we are offering you tell me" the indica of the marked inhaler becomes the data metric. Results might be: Subject identified rose aroma when presented sample #8 on the left nostril and identified the weaker rose sample #6 on the right nostril.

Alternatively, more than one aroma and/or concentration may be presented.

Controlling the presentation of aroma may be done in a number of ways, each with advantages and disadvantages which may be mitigated with proper protocols and advanced device design.

1. Testing olfactory acuity using a contained, channeled and controlled aroma source has the advantage of removing the skewing effect of the movement of room air due to air conditioning, heating and the breathing of the patient and the researcher in the testing space. These are experimental control methods completely lacking in the conventional Smith method of measuring the distance from an open plume of aroma to the nose. The aroma concentration is thus more consistent, controllable and the results more repeatable when the aroma is contained and directed into a nostril. Containing the aroma source and directing it into the nostril of the test subject allows a precisely measured presentation of aroma containing air, with the cognitive threshold sensitivity scored or quantified numerically in a number of ways. The aroma concentration is thus more consistent, controllable and the results more repeatable when the aroma is contained and directed into a nostril. Containing the aroma source and directing it into the nostril of the test subject allows a precisely measured presentation of aroma containing air, with the cognitive threshold sensitivity scored or quantified numerically in a number of ways.

2. The time in seconds between control air with no aroma present and a controlled increasing concentration of aroma (s) becoming detectable and/or identifiable is a useful metric. When the test is done sequentially for both nostrils using the same device and same aroma source, the ratio of aroma sensitivity, left vs right, may be accurately tested by using time as the metric measured to reach the relevant threshold. The nostril that takes longer or requires a higher level of aroma to recognize the presence of the aroma is the weaker nostril. A reset period between screening events may be required if only one aroma is used, e.g., in increasing concentration. This test methodology for pure odorants as well as for odorants in a screening test and dependent upon the goal of the test.

3. The number of breaths it takes to recognize the presence of an aroma being presented beginning with breathing controlled air with no aroma present is a potentially useful testing metric that has the advantage of not even requiring a clock. A reset period between screening events is required since only one aroma is being used. This testing methodology may be used for pure odorants and odorants, depending on the testing goal.

Note that time and/or breaths may both be measured and evaluated.

4. Cascading a series of aromas, either pure odorants or odorants, presented to a single nostril where the cumulative number of seconds or the number of breaths required to cognitively realize that an alternative aroma(s) is/are presented generates meaningful data and can quantitatively rate the relative performance of the two nostrils. Using at least two aromas presented one after another makes a reset period between events unnecessary, which will save time administering the screen using this method. Note that the series of odorants or pure odorants presented may comprise a single odorant or pure odorant with successively increasing concentrations.

Of all methods of aroma screening noted, the lack of a reset period between aroma presentations is particularly significant. However, alternate embodiments may include a reset period between aroma presentations or introductions. When a plurality of aromas are presented sequentially, the olfactory nerve and brain can only concentrate on one aroma at a time due to the phenomena of "olfactory nerve dissonance".

5. Odor identification tests generally contain a plurality of familiar aromas which may be cognitively challenging to demented patients who struggle to find the word in their failing memory that describes an aroma that seems familiar to them, but is hard to place its name. Simply asking someone to note when the present aroma changes to a fresh aroma, as in the cascading screen, without being required to name the aroma is less taxing cognitively.

In some embodiments, at least one pure odorant may be presented to a patient's nostril using serially (or otherwise) increasing concentrations of a single pure odorant, without requiring the subject to identify any of the aromas. In the case of pure odorants, the pure odorant detection threshold is met when the subject indicates a relevant response. This technique may also be used for odorants in a general screening test and involve the pure odorant detection threshold. Alternatively, the patient may be asked to specify when they know what the odorant is, thereby reaching the pure odorant identification threshold. Similar thresholds may be employed for odorant testing as discussed herein.

Cascading a sequence of a plurality of aromas (pure odorants or simply odorants) without (or with) a pure air reset period between aromas also scales the relative olfactory thresholds of the nostrils and has distinct advantages. The aromas may be presented manually where the aroma device is advanced to present a fresh aroma as the previous aroma is consumed or the device may be mechanically spring loaded, where the aromas are changed at the push of a button by the test subject during the screen. Alternatively, more than one device may be used to present the more than two odorants, or pure odorants, or serially increasing concentrations of a single odorant or pure odorant, to the patient.

Turning now to aroma screening protocols for offering a stepped concentration method, as described above. Some of the parameters of interest are, considerations of the medical history of the patient, the potential use of blank aroma units to be offered first, the specific aroma used, the increasing concentration steps used, the device used for presenting the set of test concentrations, the clinical method of preforming the test, the efficacy of using bypass air in the nostril not being tested, nasal airflow testing qualifications, disposable sanitary tip advantages, detecting inhalations, cleansing breaths between aroma samples, environmental consideration of the clinical space, the interpretation of the test data and the method of recording the data.

The pure odorant used for neurological testing in recently published studies have been Peanut Aroma, Peppermint, Vanilla and Rose. Theoretically, any olfactory specific odorant can be used to detect a differential for sensitivity between nostrils. Peanuts are unfortunately a deadly allergen to some people and the essential oil of peanuts is so thick it is not strongly aromatic unless the oil is extracted using exotic $CO_2$ reduction methods. Theoretically any olfactory specific odorant without significant trigeminal contamination may be used to detect a lateral differential in olfactory nerve condition.

The Figures show a nasal inhaler device 100 configured to hold a specific aroma, i.e., a specific odorant, or specific pure odorant, of a predetermined concentration therein. FIG. 1 illustrates one embodiment wherein the subject is testing her right nostril while physically closing her left nostril. Each nasal inhaler device 100 is designed to be presented to a subject's first nostril, either left or right, and then the other nostril. It is preferred that the subject's right nostril be designated as the first nostril, though not required.

As shown in the Figures, the nasal inhaler device 100 may comprise a unique keyed identifier or indicia 102, illustrated as sequential numbers, which enable a keyed identification of the specific aroma source "A" held within a specifically numbered inhaler device 100. The keying identifier 102 enables the test to proceed in a pre-defined or pre-determined order of aromas/presentations to maximize efficacy and accuracy. Other substantially equivalent methods for pre-defining and maintaining a testing order will be known to the skilled artisan, each of which are within the scope of the present invention.

Randomization may be employed by using non-sequential letters or numbers to avoiding disclosing expected order of the indicia. The computer or paper test page could call out the order of samples to be offered with a sequential protocol.

Referring now to the Figures, embodiments of the nasal inhaler device 100 comprise a lower inhaler body 104 defining an aroma storage compartment 106 therein. Device 100 further comprises an upper cover 105 comprising a upper housing 109 and a tip 110 that may be in certain embodiments transparent. Tip 110 comprises a nasal aperture 114 therethrough, thereby enabling fluid communication between the subject's nostril during testing and the check ball compartment 108 defined within and by the upper housing 109 and tip 110. The nasal aperture 114 is shown without a valve, though a one-way valve of a form well known to the skilled artisan may be provided within the nasal aperture 114, wherein inhalation flow is allowed and exhalation flow is prevented through the nasal aperture.

Figure 3A:
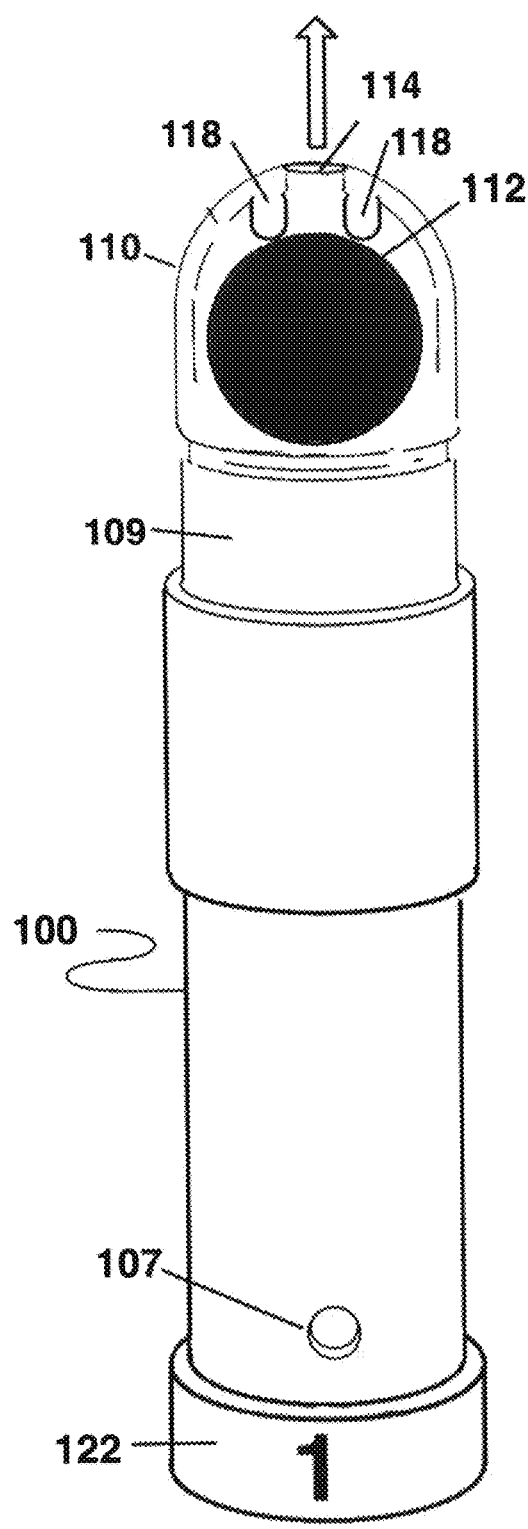
FIG. 3A illustrates a front perspective view of one embodiment of the present invention.
Figure 3B:
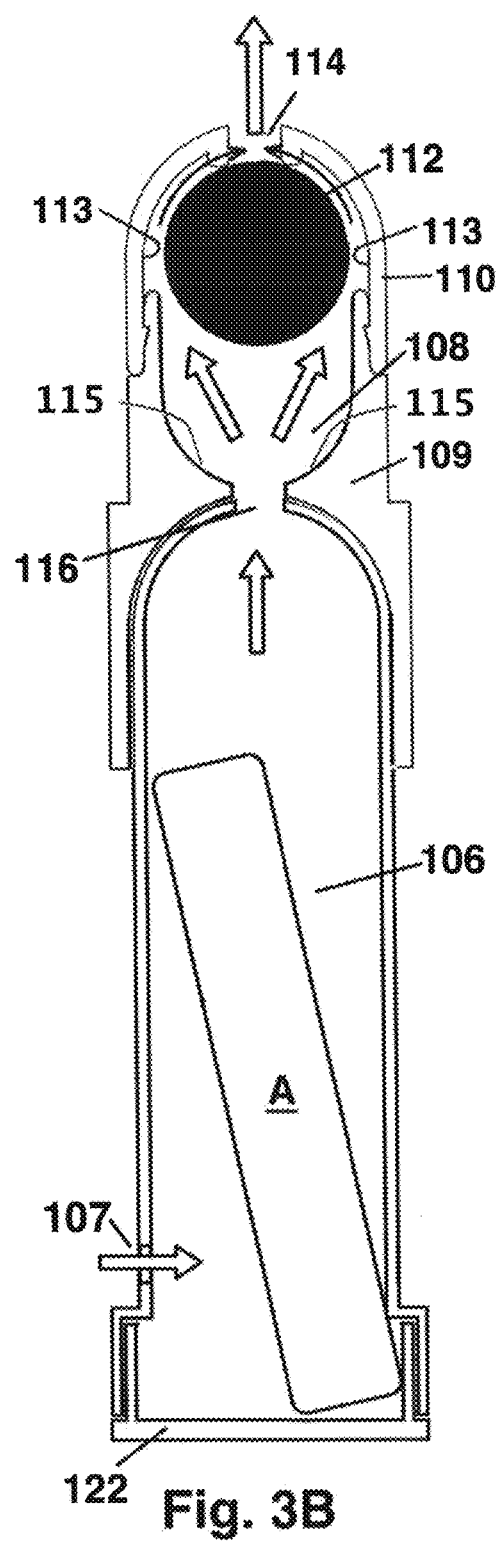
FIG. 3B illustrates a cross-sectional view of the embodiment illustrated in FIG. 3A.
Figure 4A:
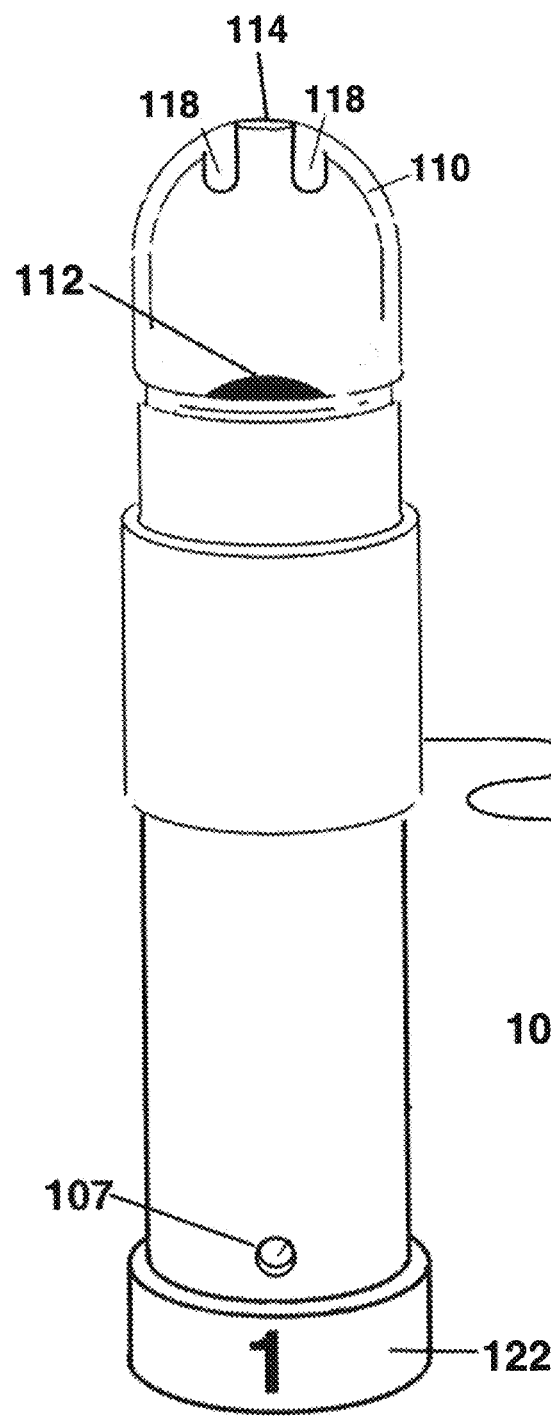
FIG. 4A illustrates a front perspective view of one embodiment of the present invention.
Figure 4B:
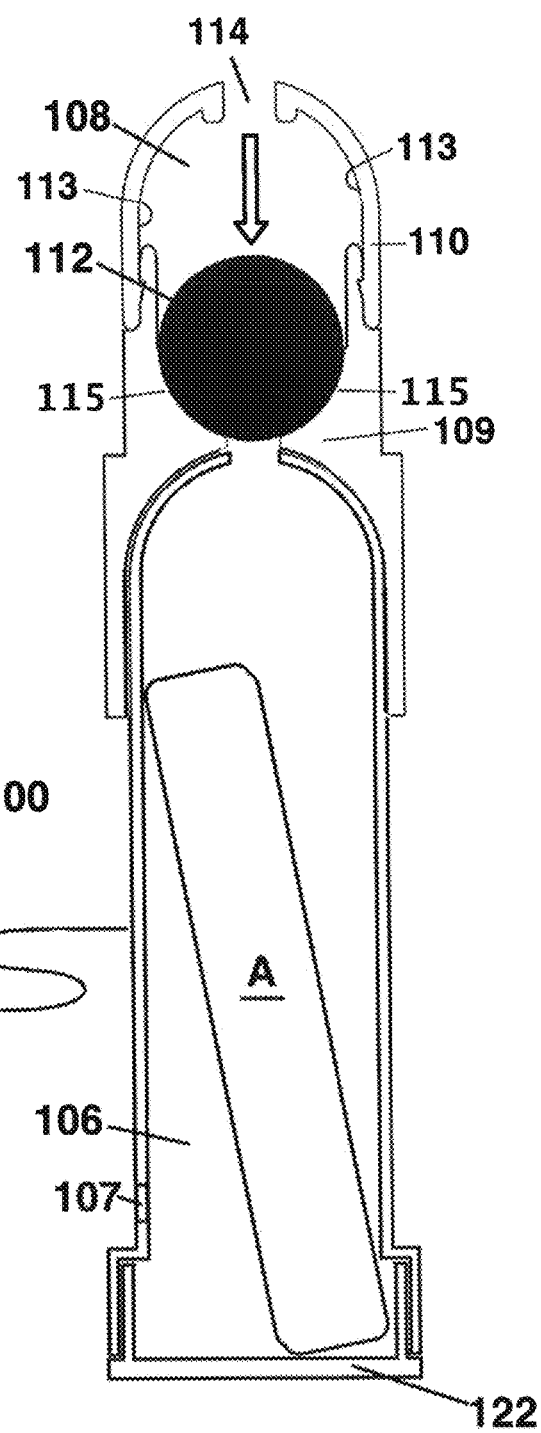
FIG. 4B illustrates a cross-sectional view of the embodiment illustrated in FIG. 4A.

Together, the upper housing 109 and tip 110 define the check ball compartment 108 on the interior of the upper housing 109 as seen in cross-section in FIGS. 3B and 4B. A check ball 112 may be translatably contained within the check ball compartment 108, the check ball 112 responsive to pressure changes and the resulting upwardly moving air flow forces generated by the test subject during an inhalation. The check ball compartment 108, in combination with the check ball 112, is dimensioned to permit the check ball 112 to move upward during inhalation at the nasal aperture 114 and to provide a gap or spacing between the upwardly moved ball 112 and the inner walls 113 of the check ball compartment to provide an avenue for air flow around the ball 112. This spaced arrangement between the inner walls 113 of the check ball compartment 108 and the check ball 112 works in combination with the spacer(s) 118 of the tip 110 to provide air flow channels during inhalation by preventing the check ball 112 from blocking nasal aperture 114.

During periods when no inhalation is occurring at the nasal aperture 114, check ball will drop down to the bottom of the check ball compartment to cover the aperture 116 between check ball compartment 108 and aroma storage compartment 106, either as a result of the force of gravity and/or the downward flow of exhaled air from the test subject through the nasal aperture 114. Thus, the portion of the bottom of the check ball compartment that contacts the resting check ball 112 during non-inhalation periods defines a check ball seat 115. In certain embodiments, the chock ball seat 115 comprises a complementary shape or profile, and size, to that of the check ball 112 to provide a sealing engagement therewith during non-inhalation periods.

As will now be clear, when the check ball 112 engages the check ball seat 115, the aperture 116 between the check ball compartment 108 and the aroma storage compartment 106 is blocked by the presence of the check ball 112. When the check ball 112 disengages from the check ball seat 115, the aperture 116 is not blocked and air is allowed to flow therethrough. As a result of this structural arrangement, air flow is allowed in only one direction, in the inhalation direction, from the aroma storage compartment 106 to the check ball compartment 108, with air flow in the opposing direction blocked and/or disabled by the engagement of the check ball 112 with the check ball seat 115.

In other embodiments, a one-way valve may be employed to allow inhalation air flow while preventing exhalation air flow through device 100.

In certain embodiments, the tip 110 may be removably attached to the upper housing 109, enabling removal after use. A new tip 110 may then be attached to the upper housing 109 to allow a new test subject to reuse the test device 100. In this case, the tip 110 may be referred to as a sanitary tip 110. Therefore, in some embodiments, the entire upper cover 105 may be disposable while in others, upper cover 105 may comprise a multiple use device that may be used, removed and stored and/or disposed. Acceptable attachment methods are well known and include without limitation, friction fit, threaded engagement, clips, snaps, complementary engagement surfaces and the like, all of which are within the scope of the present invention.

Alternatively, the entire upper cover 105, which comprises the upper housing 109 and the tip 110, may be attached to the inhalation body 104 after use to enable removal and storage or disposal after use. A new upper cover 105 comprising the upper housing 109 and the tip 110 may then be reattached to the reusable inhalation body 104 in preparation for a new test subject. Acceptable attachment methods are well known and include without limitation threaded engagement, clips, snaps, complementary engagement surfaces and the like, all of which are within the scope of the present invention.

In other embodiments, the unit 100 may be used for a single patient and disposed after use.

The aroma storage compartment 106 is defined within the inhaler body 104 and is sized and shaped to hold the stored aroma source "A" therein. The aroma storage compartment 106, and the stored aroma source "A" therein, may be in fluid communication with one or more inhalation ports 107 disposed through the walls of the inhaler body 104. The inhalation port(s) 107 are in further fluid communication with the external atmosphere, or clean air that is substantially free of the tested aromas so that clean air may be drawn into the aroma storage compartment 106 for aroma-infusion by contact and/or interaction with the stored aroma source A during an inhalation.

When the inhaler body 104 and upper cover 105 are operatively engaged, the aroma storage compartment 106 is placed in switchable fluid communication with the check ball compartment 108 comprising one-way air flow as described above. The fluid communication may be achieved in a number of ways all known to the skilled artisan. The illustrated fluid communication between aroma storage compartment 106 and check ball compartment 108 is achieved by means of the aperture 116 formed between, and defined by, the assembly of the upper housing 109 and the inhalation body 104. The aperture 116 is defined by an opening at the floor of the check ball compartment 108 in combination with an aligned opening in the top or ceiling of the aroma storage compartment 106.

The aperture 116 comprises a position, size and shape. In the illustrated case, the position enables the check ball 112 to rest on the aperture 116, covering, and closing, the aperture 116 from airflow therethrough. Because the ball 112 is circular, the aperture 116 may also a circular shape and the size is further adapted so that the check ball 112 covers the aperture 116 substantially completely when resting thereon. In this embodiment, the check ball 112 acts as a one-way valve, allowing upward flow as the ball 112 rises in response to air flow generated by inhalation at the nasal aperture 114 as best shown in FIGS. 3A and 3B. When the inhalation-generated air flow ceases, the ball 112 drops down to cover the aperture 116, thus preventing downward airflow from the check ball compartment 112 into the aroma storage compartment as shown in FIGS. 4A and 4B.

Accordingly, in some embodiments, the check ball 112 is adapted to achieve a resting position during a period where no inhalation is occurring at nasal aperture 114 as shown in FIGS. 4A and 4B. Stated differently, during a period of exhalation by the test subject at the nasal aperture 114, check ball 112 will be driven downward to achieve the resting position, either by force of gravity and/or any airflow directed down through the nasal aperture 114 by the test subject's exhalation. Check ball 112 is further adapted to achieve an active position, wherein the check ball 112 is translated upward through the check ball compartment 108 and away from the check ball seat 115, during a period of inhalation at the nasal aperture 114 that creates sufficient upward airflow to cause the check ball 112 to rise from the resting position. Thus, check ball 112 functions as a valve, allowing inhalation air flow and preventing exhalation air flow through the device 100.

The aperture 116, in alternate embodiments, may comprise a one-way valve that allows airflow generated by inhalation at the nasal tip 114, but prevents exhalation airflow from through the device 100.

Figure 5:
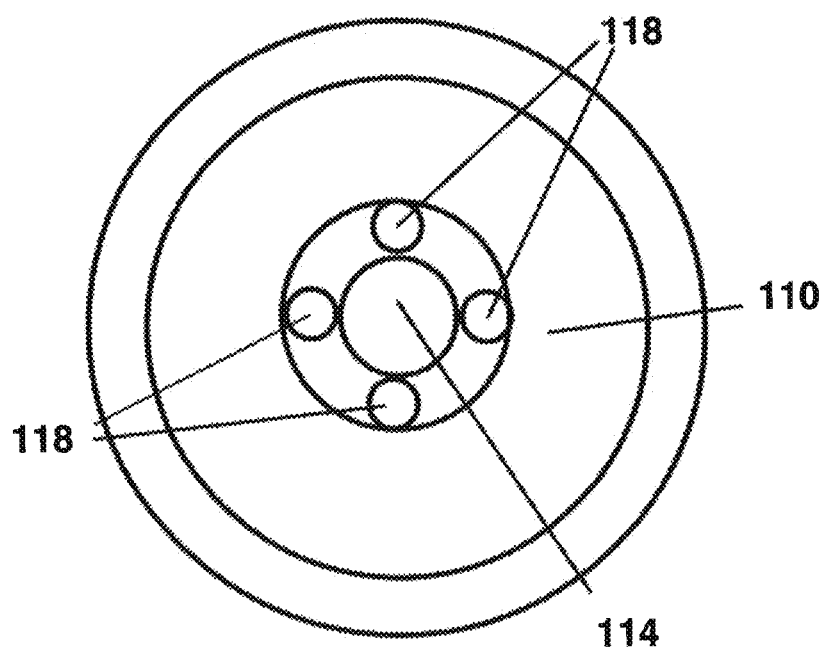
FIG. 5 illustrates a bottom view of a tip of the embodiment illustrated in FIGS. 4A and 4B.

The check ball 112 is adapted and enabled, in response to the upward air flow forces generated during inhalation, to rise up through the check ball compartment 108 until engaging at least one stop spacer 118 disposed proximal the nasal aperture 114 and protruding a distance into the check ball compartment 108. FIG. 5 illustrates a bottom view of the tip 110 with four stop spacers 118 equally spaced around the nasal aperture 114. Other configurations are possible and within the scope of the present invention.

The at least one stop spacer 118 spaces the ball 112 from the nasal aperture 114 a distance sufficient to allow and enable the air flow to continue through the nasal aperture 114 during inhalation; the stop spacer(s) 118 provided to prevent the rising check ball 112 from blocking the nasal aperture 114. The check ball 112 will then drop down to the bottom of the check ball compartment 108 when the upward force is removed, thereby covering and closing the aperture 116 in certain embodiments and eliminating the fluidly communicating airflow between the atmosphere, the aroma storage compartment 106, the check ball compartment 108 and the nasal aperture 114 so that no further infused air reaches the subject's nostril during exhalation.

Thus, the air flow during an inhalation generating sufficient pressure and force to raise the check ball 112 within the check ball compartment 108 comprises clear or clean air entering the one or more inhalation ports 107 through the inhalation body 104 into the aroma storage compartment 106 where the designated specific aroma source A resides. The inhaled air contacts the specific aroma source A within the aroma storage compartment 106 whereupon the inhaled air becomes infused with the aroma of the stored aroma source A. The aroma-infused air then, also motivated by the inhalation of the subject, moves through the aperture 116, which has been opened by the upward rise of the check ball 112, and into the check ball compartment 106.

Because the check ball 112 is raised away from the aperture 116, and is spaced away and apart from the inner walls 113 of the check ball 112, channels of airflow are provided between the check ball 112 and the inner walls 113 defined within the check ball compartment 112 as best shown by the arrows in FIG. 3B. Note that the illustrated inner walls 113 of the check ball compartment 112 are curved toward the nasal aperture 114 to, inter alia, aid in communicating and focusing the inhaled air toward and through the nasal aperture 114. Eventually, the infused air does pass through the nasal aperture 114 and into the nostril of the inhaling subject. When the inhalation is complete, the air pressure-driven upward force ceases and the check ball 112 drops back to cover the aperture 116, closing the fluid communication airflow between the subject's nostril and the aroma storage compartment 106 and the aroma-infused air created and held therein.

In certain embodiments, the upper cover 105, or portions thereof, may be constructed of a clear or transparent material such as a plastic to enable visualization of the check ball 112 movement and position to enable a test professional or partner to assist in counting the inhalations without unduly influencing the natural breathing of the test subject. Thus, in some embodiments, the tip 110 may comprise a clear or transparent material and in other embodiments at least some of the upper housing 109 may comprise a clear transparent material. Check ball 112 may comprise a color that allows visualization.

The preferred embodiment is that the check ball housing 109 is not transparent and a different color than the check ball 112 and only the nasal tip 110 is clear. This hides the check ball 112 from view when at rest and allows it to be seen only upon an inhalation as the check ball 112 is inhaled upwards out of the upper housing 109 to be easily viewed through the clear nasal tip 110.

The aroma storage compartment 106 may be further defined by a bottom section 122 that may, or may not be removable in certain embodiments. In embodiments comprising the removal of the bottom section 122, removing bottom section 122 facilitates opening of, and access to, the aroma storage compartment 106 so that an aroma source "A" may be installed, removed and/or replaced therein. In other embodiments, the aroma storage compartment 106 may be manufactured with the aroma source "A" sealed therein.

It is now clear that the rise and fall of the check ball 112 may be considered a single cycle, breath, and/or inhalation and exhalation, for purposes of designating a relative metric to be measured and analyzed for each individual subject to reach at least one of the "pure odorant detection threshold," the "pure odorant identification threshold," the "odorant detection threshold," or the odorant identification threshold" for a particular aroma. In combination with the rise and fall of the check ball 112, other metrics may be employed, e.g., time to reach the relevant threshold, time of inhalation, etc.

The rise and fall of the check ball 112 may be used as a surrogate or analog for a metric relating to the number of inhalations or breaths taken by the test subject for a specific aroma source A presented during the screening test, each breath or inhalation marked by a rising of the check ball 112 within the check ball compartment 108 away from the check ball seat 115. The number of times the check ball 112 rises away from the check ball seat 115 for each presented aroma source A, from the first inhalation to the reaching of the appropriate threshold, for of the first and second nostrils may be monitored, counted and stored for later analysis. In cases where only one breath is allowed per aroma sample, the contrasting colored check ball 112 can be easily viewed by the test giver as it rises upwards at a single inhalation without tipping off the subject that breaths are being monitored.

Figure 7:
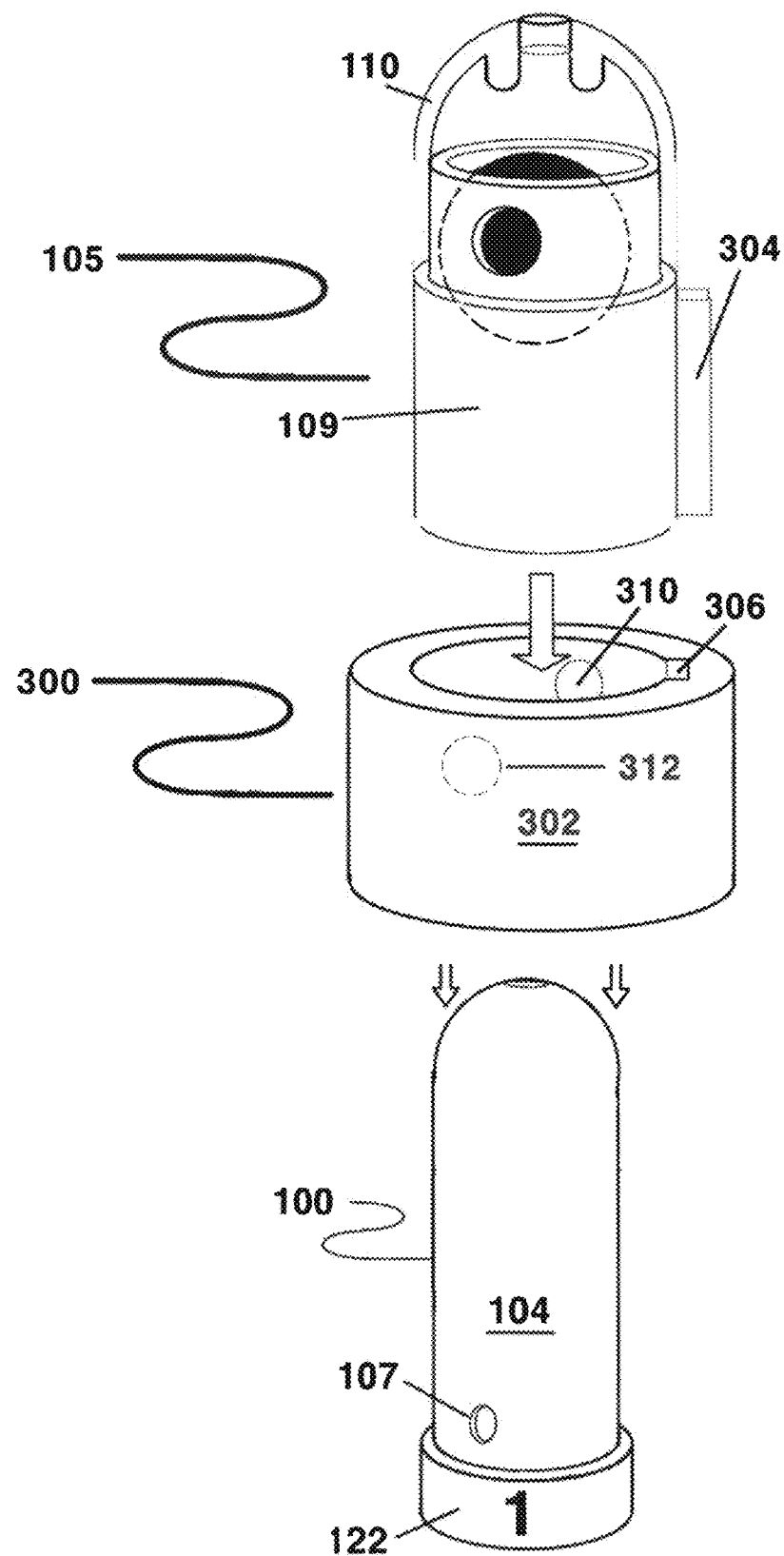
FIG. 7 illustrates an exploded view of one embodiment of the present invention.

FIG. 7 illustrates one embodiment of an automated mechanism for monitoring and capturing or recording the number of rise/fall cycles the check ball 112 moves through for each administered aroma. Thus, device 300 is provided with an upper cover 105 comprising an upper housing 109 and a tip 110 and check ball 112 within the check ball compartment 108 substantially as previously described in connection with device 100 above with several modifications. The lower inhalation body 104 is configured in the same manner as described above as well.

A detection collar 302, an exemplary embodiment illustrated as an open cylinder with substantially cylindrical walls with a lumen defined by the walls as shown, is now provided to engage and surround a portion of the upper cover 105. In some embodiments, detection collar 302 may be structurally integrated with upper cover 105. As shown, the upper housing 109 now comprises a male key element 304 that when properly aligned engages the complementary shaped female key element 306 disposed within the inner wall of detection collar 302. Upper housing 109 slides within the lumen of the detection collar 302. The detection collar 302 comprises a photo detection system comprising a light source 310, e.g., an LED, a light or photo detector 312 aligned with the light source 310, a transceiver module or the equivalent 314, all in electrical communication with a battery 316 that may be actuated with a button.

As shown the light source 310 is embedded within the detection collar 302 and adapted and configured to face the check ball compartment 108. The photo detector 312 is arranged and embedded within the detection collar 302 on the other side of the detection collar's lumen so that the photo detector 312 is aligned with, and therefore can detect, the light of the light source 310 emitted in a straight line across the check ball compartment 108, when check ball 112 is not blocking the light.

The upper housing 109 is modified now to accommodate this arrangement, comprising first and second light channels 320, 322 through at least a portion of the wall of upper housing 109, wherein the first and second light channels 320, 322, the light source 310 and the photo detector 312 all are in substantial linear alignment. Because of the keyed arrangement, the first light channel 320 will be associated with the light source 310 while the second light channel 322 will be associated with the photo detector 312 as shown.

Figure 8B:
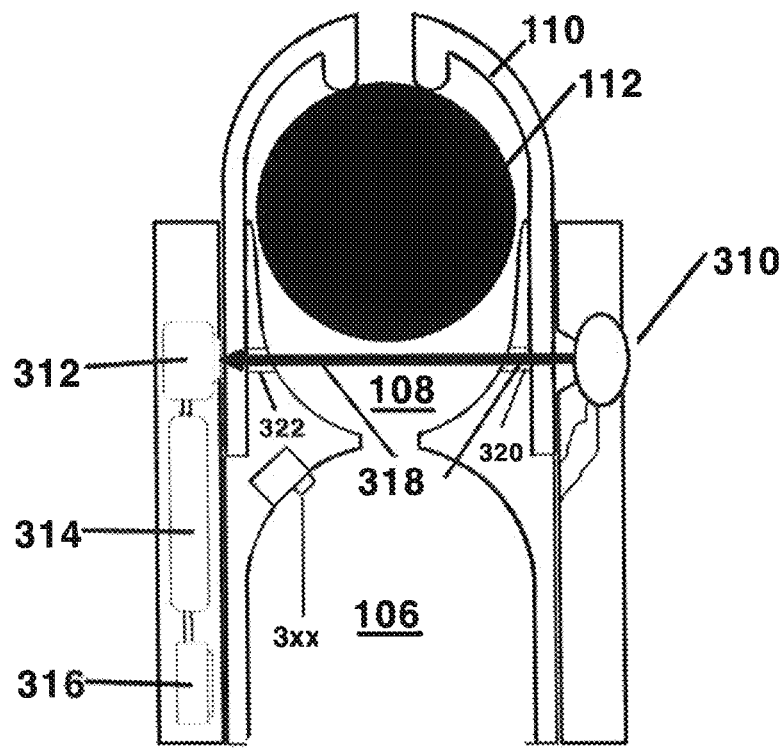
FIG. 8B illustrates a cross-sectional cutaway view of one embodiment of the present invention.
Figure 8A:
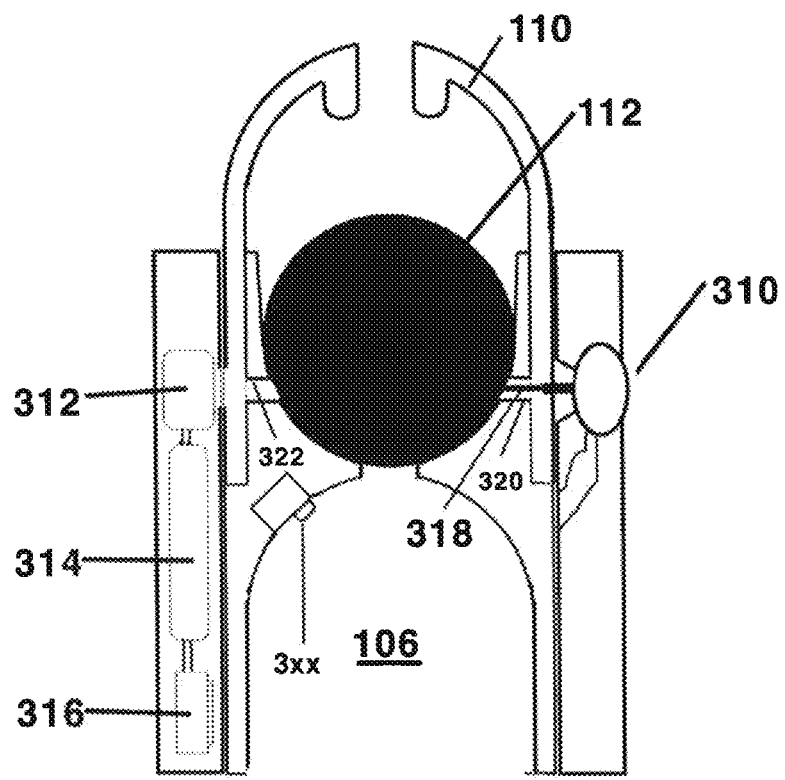
FIG. 8A illustrates a cross-sectional cutaway view of one embodiment of the present invention.

The utility of the device 300 is illustrated in FIGS. 8A and 8B. Thus, in FIG. 8A, when the light source 310 is actuated during a testing session, the light emitted along light channel 320 by light source 310 is blocked by the presence of the check ball 112 which is substantially opaque and, therefore, cannot activate the photo detector 312. This is the arrangement of the elements during an exhalation in the testing session.

However, during an inhalation and as described above, the check ball 112 rises within the check ball compartment 108, eventually rising above the level of the light beam 318 emitted by the light source 310 and transmitted through light channel 320, across the check ball compartment 108, through light channel 322 and eventually to photo detector 312 which detects the beam of light and the circuit is completed and the photo detector 312 sends an electronic pulse to the transceiver module 314. When the test subject exhales, the check ball 112 returns to its seat and the light stream 318 is again blocked from reaching the photo detector 312.

The device 300 is now arranged to transmit, via transceiver module 314, the number of activations of the photo detector 312 which is in operative communication with the transceiver module 314, correspondent to the number of inhalations by the test subject for the particular aroma being test at that moment, to an external device 317 which is arranged to receive the transmitted data and record and organize it according to at least the test subject's identifier and the particular aroma that is related to the generated data. The external device 317 may comprise a programmable tablet, smartphone, computer or similar device positioned locally or remotely, connected and accessed by the internet to the transmitted data. Further, the external device may comprise a server that is located locally in relation to the transceiver module 314 or the server may be cloud-based and remotely located. In certain embodiments the external device 317 may comprise executable instructions that enable the external device 317 to receive and interpret the data transmitted from the transceiver 314 as the number of breaths taken, as well as automatically monitoring and recording the time taken from first inhalation to the reaching of the relevant threshold, i.e., odorant detection, odorant identification, pure odorant detection, pure odorant identification, for each aroma source A and for each nostril.

Thus, the device 300 substantially automates the counting of breaths and/or time of each test point in the sequence, removing these as a variable and as a cause of concern for the test administrator and for the test taker. In fact, device 300 now makes it possible for a person to conduct a test with a high degree of accuracy and without necessarily requiring the aid of a test administrator or testing professional.

Alternatively, automated counting of the rise/fall movement of the check ball 112 may be done using a variety of mechanisms. For example, actuatable microswitches, induction coils or RF chip detection may be employed to monitor whether or not the check ball 112 is seated within the check ball compartment on aperture 116, with transmission via a radio link or other well-known transmission mechanism to a programmable computing device such as a smart tablet, smart phone or other computing device. Still more alternatively, a photo detection circuit may be used to detect the position of the check ball as described above, with subsequent transmission of the detection data via a radio link or other transmission mechanism to a programmable computing device. These data may be subsequently stored within a generally centralized database that may be connected with the internet and may be cloud-based or otherwise remotely located from the test site.

Figure 2A:
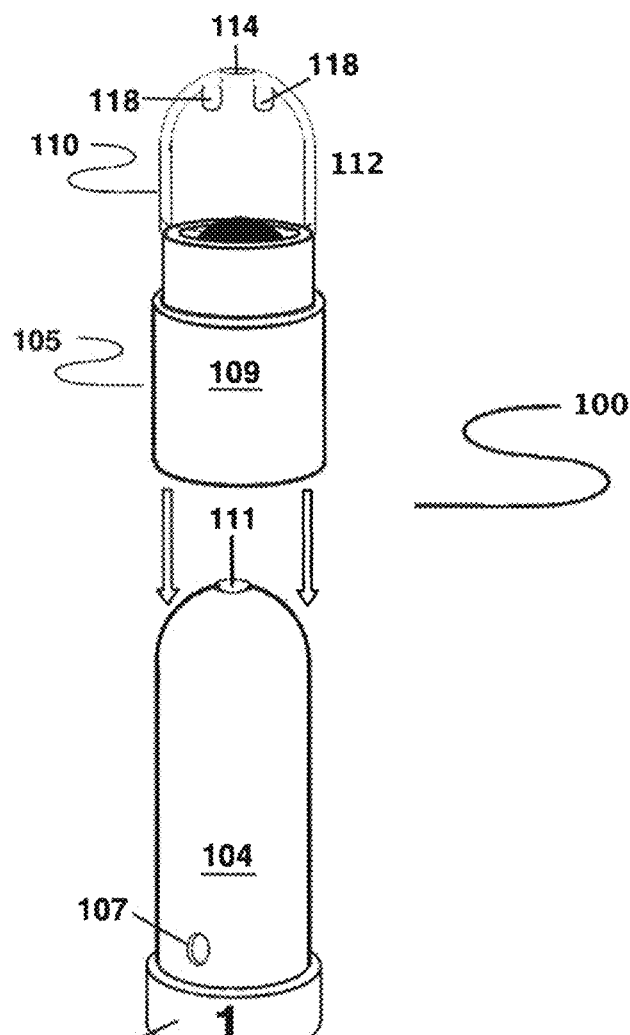
FIG. 2A illustrates a front perspective and partially disassembled view of one embodiment of the present invention.
Figure 2B:
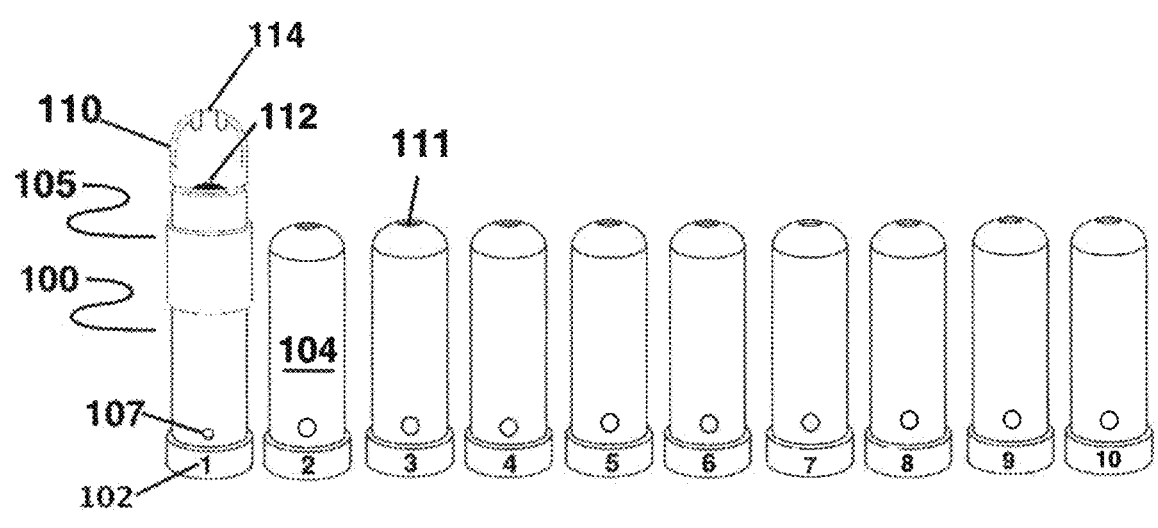
FIG. 2B illustrates a front perspective view of a kitted embodiment of the present invention.

Turning now to FIGS. 2A and 2B, more than one lower inhalation body 104 may be provided in a kit form, with pre-selected or predetermined aroma source "A" pre-loaded therein and together with at least one potentially disposable upper cover 105. This kitted arrangement may then comprise a screening set of aromas, either pure odorants, odorants, or in certain cases pure odorants and/or odorants may comprise the screening set. The pre-selected and pre-loaded aroma sources "A" may be arranged in a particular predetermined test sequence and may, or may not, all be unique and non-repeating in the test sequence and may comprise a diluted sequence of progressively increasing concentrations of at least one pure odorant or odorant and may further comprise at least one blank or control with no aroma, or in some cases with an odorant that will stimulate both the $1^{st}$ and the $5^{th}$ cranial nerves that may be presented at a concentration that the vast majority of people will be able to either detect or identify.

The user will then, as shown in FIG. 2A, begin the testing sequence by selecting the device with keyed indica "1". In alternate embodiments, the lower inhaler body with indicia "1" may be presented in engagement with the upper cover 105 or the upper cover 105 may be provided apart and separated from the lower inhalation body "1". In either case, the device 100 is assembled in general conformance with the device 100 of FIG. 3A and the testing sequence described above is undertaken for a first nostril until one of the odorant detection threshold, the odorant identification threshold, the pure odorant detection threshold, or the pure odorant identification threshold is met. The type of defined threshold used depends on whether the aroma source is an odorant or a pure odorant and whether the testing is designed and instructed to simply detect an odor or whether identification of the odor is required. The testing may further comprise a metric that comprises one or more of the time (in seconds, e.g.,) from the first inhalation to the reaching of the relevant threshold and/or the number of inhalations or breaths required to meet the relevant threshold. The test may then be conducted for device 100 with indicia "1" for the second nostril until the relevant threshold is met.

The method of testing may be different for pluralities of aroma concentration and identifications. Once the testing is completed for device 100 with indicia "1", the upper cover sanitary tip assembly 105 may be disengaged from the lower inhaler body marked as "1" and switched into engagement with the next higher concentration inhaler body 104 in the testing sequence, as illustrated having an indicia of "2" and then sequentially for each of the plurality of aromas in the kit. The testing process for the first nostril is then repeated for the second nostril. Note that the indicia may comprise one or more of letters, numbers and/or markings that allow sequential or randomized screening methods.

Further, the indicia may comprise a scannable code such as a QR or UPC code that, when scanned, identifies the device 100 and aroma therein, and in some cases, the patient undergoing the test.

Once the testing is completed for device 100 with indicia "1", the upper cover 105 may be disengaged from the lower inhaler body marked as "1" and switched into engagement with the next lower inhaler body 104 in the testing sequence, as illustrated having an indicia of "2" and the testing process repeated for the first nostril and then for the second nostril. This process will be repeated for each successive lower inhaler body 104 in the testing sequence until the last one is reached.

Figure 6A:
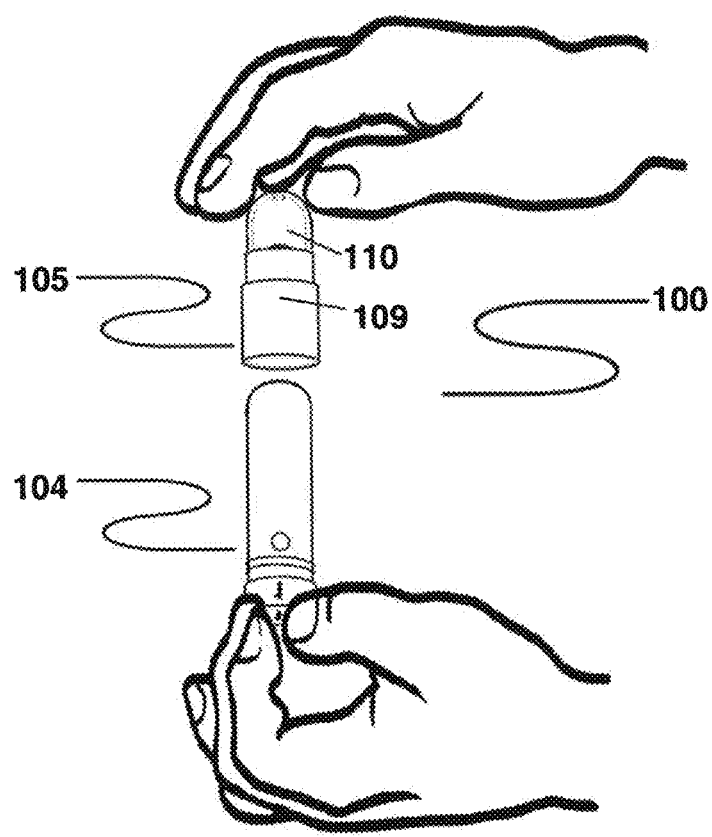
FIG. 6A illustrates one embodiment of the present invention.
Figure 6B:
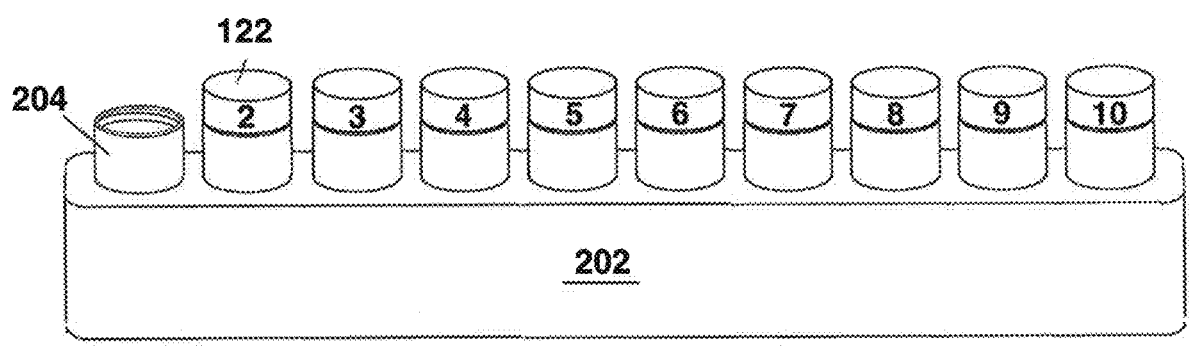
FIG. 6B illustrates a kitted embodiment of the present invention.

An alternative embodiment of a kit is illustrated in FIGS. 6A and 6B. There, kit comprises a base 202 with a series of receptacles 204, each receptacle 204 adapted to sealingly engage, one lower inhalation body 104. A threaded engagement is illustrated but other sealing engagements are within the scope of the present invention. At least one upper cover 105 is provided with this kitted embodiment. At least one potentially disposable sanitary tip assembly upper cover 105 may be provided with kitted embodiments.

The lower inhalation body 104 is shown in FIG. 6B installed within the receptacles 204 and oriented so that the top opening 111 is arranged and held within the receptacle with the bottom section 122 sealingly engaging the respective receptacle 204 and so that the keyed indicia 102 are visible and sealing the aroma source A within the now-sealed receptacle 204 and lower inhalation body 204 arrangement. The sealing engagement is needed to prevent the aroma source "A" stored within the inhalation body 104, specifically within the aroma storage compartment 106 as discussed above, from drying out if provided in a relatively exposed wet form such as a moistened wick or other material.

In this kitted embodiment, upper cover 105 may be provided separately, and in some embodiments sequentially, for use with each sealed inhalation body 104 in the keyed indicia sequence generally following the testing procedure described above, but with the following modifications.

Disengaging the first inhalation body 104 from its sealed engagement with receptacle 204 and removing the first inhalation body 104 therefrom now enables the upper cover 105 to be aligned and engaged with the lower inhalation body 104 as discussed above and in general conformance with the device 100 illustrated in FIG. 3A. The test with the device 100 with the first keyed indicia 102 in the testing sequence, e.g., "1" may now proceed, with replacement of the first lower inhalation body 104 in its sealed engagement with receptacle 204 and repeating these steps with the second lower inhalation body 104 in the testing sequence, e.g., keyed indicia 102 indicated as "2", beginning with engaging the second lower inhalation body 104 in the testing sequence with the upper cover 105 to assemble a new device 100 and continuing with the testing process as indicated above. These steps are repeated for each additional successive lower inhalation body 104 sealed in the base 202 until the aroma source A in the last inhalation body 104 having the last keyed indicia 102 in the testing sequence is tested.

Thus, more than one, or a plurality, of nasal inhaler devices 100 may be provided to comprise a screening set of aromas, either pure odorants, odorants, or in certain cases pure odorants and/or odorants may comprise the screening set. The aromas may be arranged in a particular predetermined test sequence and may, or may not, all be unique and non-repeating in the test sequence.

When using the screening method of a stepped concentrations of one aroma, should a concentration of aroma be detected by the patient, the test may continue by stopping the sequence for the first nostril and turning to the other nostril to compare the minimum detectable concentration of the second nostril. Once the pure aroma is detected by either nostril, there is no reason to continue to offer stronger samples to that nostril. Aroma detection fatigue and human aroma latency from exposure to strong odorants are avoided by stopping each test at the lowest concentration detectable.

Another embodiment of the device 100 comprises the inhalation body 104 and the upper housing 109 manufactured as a singular unit, without means to separate them and either provided individually or in a kitted group with a predetermined testing sequence or order. In this case, the tip 110 may be removably attached to the singular unit for the reasons described above. Still more alternatively, the device 100 may be manufactured as fully assembled and ready for use, including the aroma source A stored within lower inhalation body 104, without ability to separate or remove any of the components. In this case, the device 100 may comprise a single-person test device that may be wiped clean after each use or simply discarded as a one-use device.

An alternate, and preferred, two-nostril embodiment device 400 is shown in FIGS. 9A-9D and comprising an active section 402 and a passive section 404 that may be removably connected and substantially aligned and spaced apart to allow alignment with a patient's right and left nostril at the same time as illustrated. The active section 402 comprises the stored aroma source "A" as discussed herein and further comprises a function and structure as that of device 100 also discussed herein. The passive section 404 may comprise a housing similar to device 100 but comprising a second check ball 406 therein. Check ball 406 is responsive within the lumen 408 of passive section 404 such that inhalation through the nasal aperture 410 creates airflow therethough and in combination with the lower section aperture 412 by drawing atmospheric air through lumen 408. In turn, check ball 406 will rise to a level within lumen 408 that is proportional with the inhalation force applied by the patient at nasal aperture 410. As shown, a "pass" line may be used to determine if the patient's ability to inhale with sufficient force is adequate for the test.

Figure 9A:
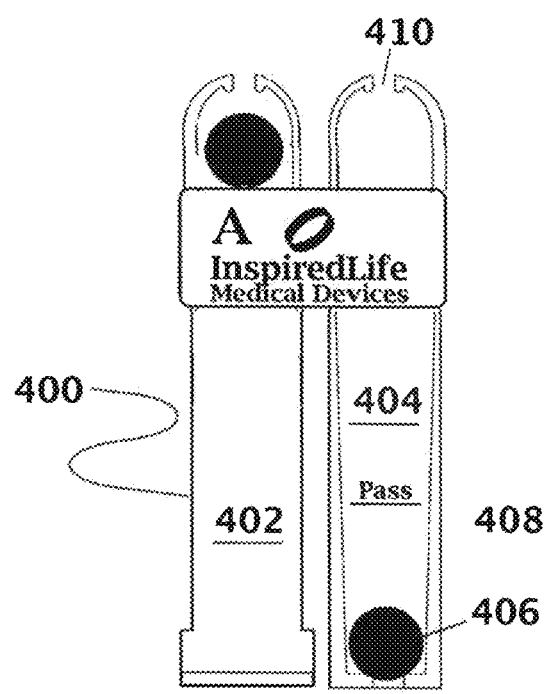
FIG. 9A illustrates a side front view of one embodiment of the present invention.
Figure 9C:
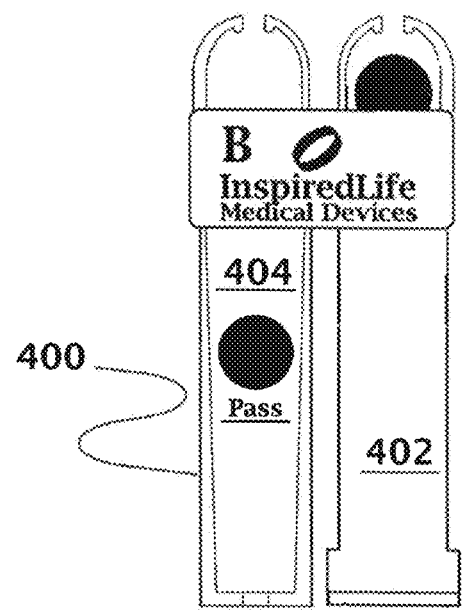
FIG. 9C illustrates a side rear view of the embodiment of FIG. 9A.
Figure 9B:
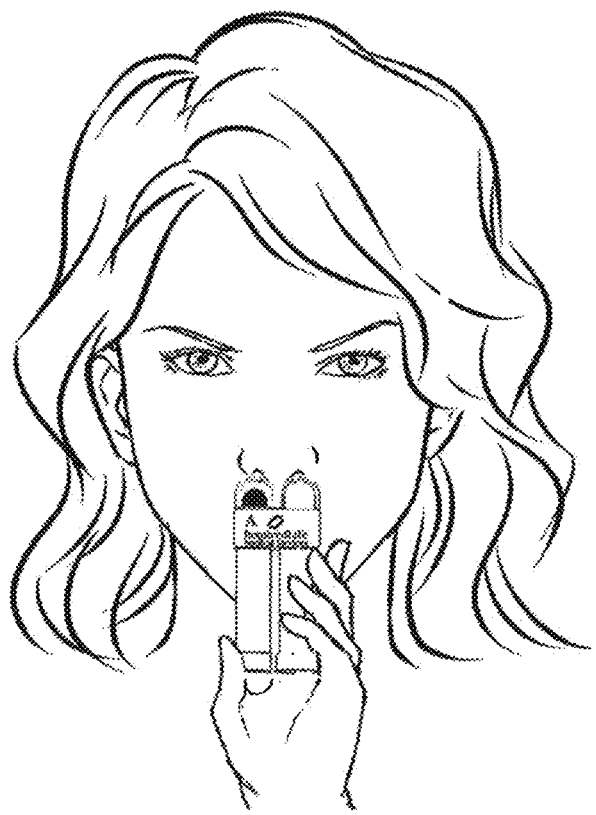
FIG. 9B illustrates the embodiment of FIG. 9A in exemplary use.
Figure 9D:
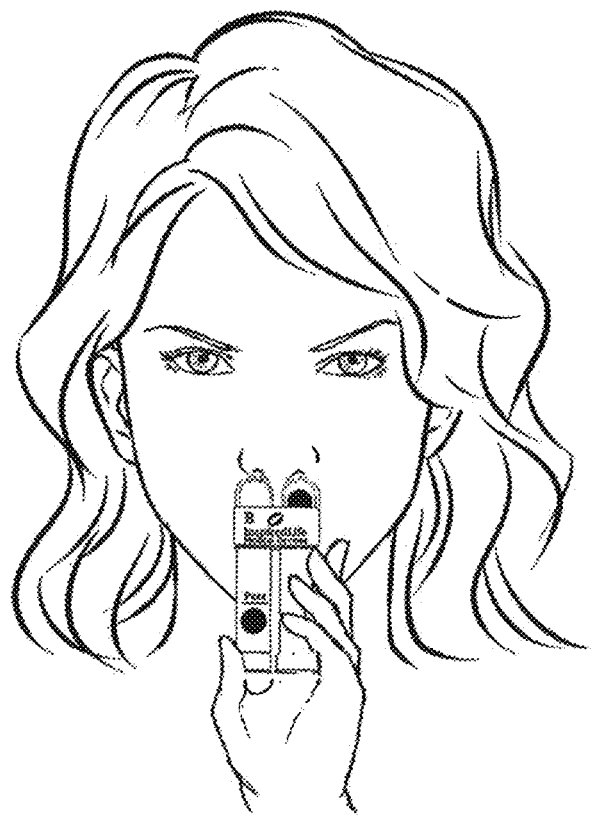
FIG. 9D illustrates the embodiment of FIG. 9C in exemplary use.

The device 400 is used as in FIGS. 9A and 9B to test the patient's right nostril by arranging the active section 402 with the right nostril. At the same time, the patient's left nostril is evaluated for sufficiency of inhalation force by engaging the left nostril with the passive section 404. When the test is completed, the device 400 is turned 180 degrees as in FIGS. 9C and 9D and the testing repeated, this time with the active section 402 engaging the right nostril and the passive section 404 engaging the left nostril.

The passive section 404 may simply comprise a pass/fail line as shown or may comprise a scale to use to measure and record the level of the check ball 406 rise during inhalation. These data may be used to scale the aroma test results.

Figure 10A:
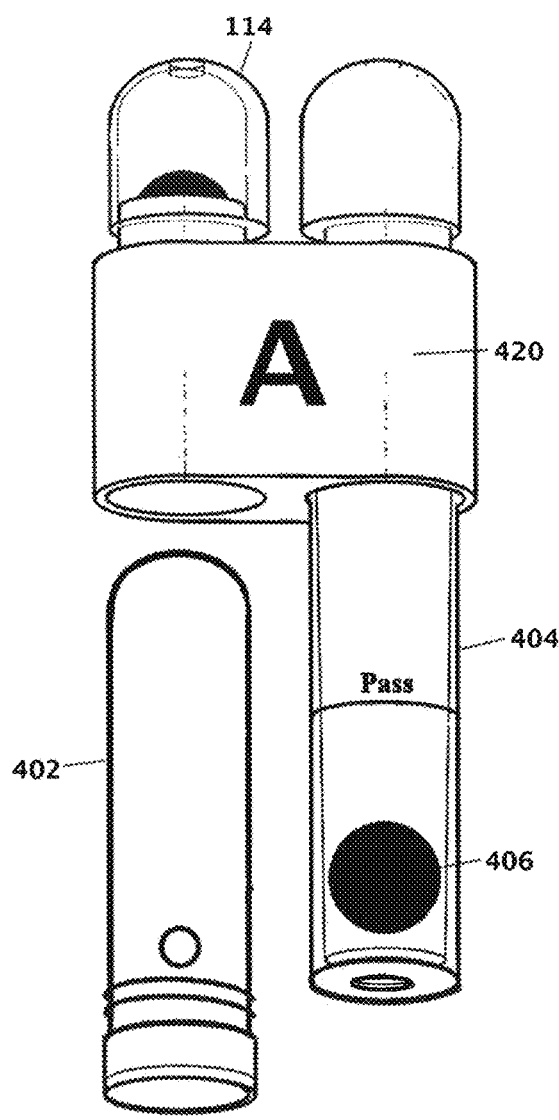
FIG. 10A illustrates a front perspective view of a partially assembled embodiment of the present invention.
Figure 10B:
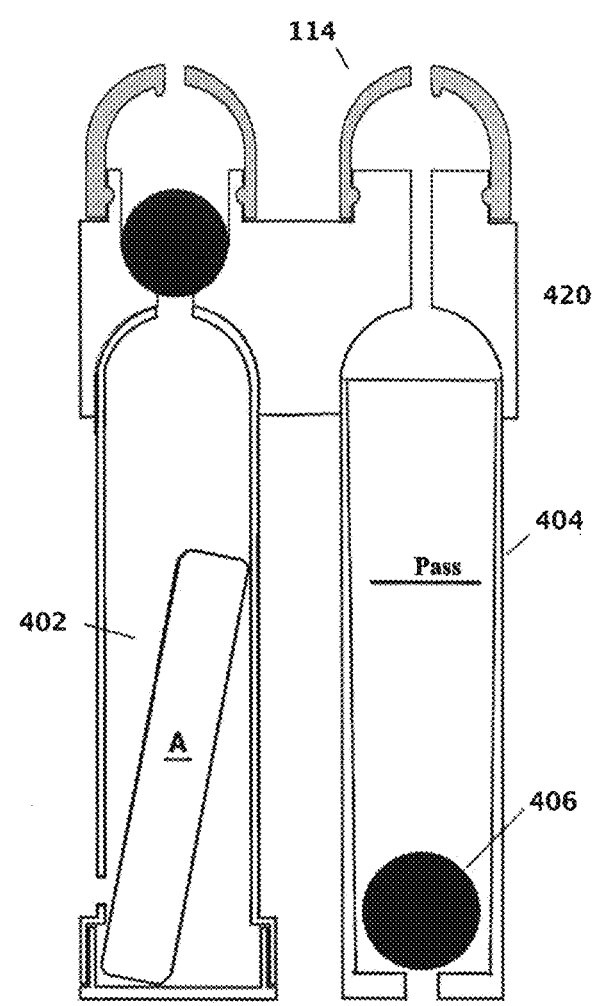
FIG. 10B illustrates a cross-sectional assembled view of the embodiment of FIG. 10A.

One embodiment of the device 400 comprising passive section 404 and active section 402 is shown in FIGS. 10A and 10B, each with nasal tips 114 and further comprising a retainer 420 with apertures therethrough to allow the patient to inhale through both nostrils. One nostril will breath the aroma-infused air presented by the active section 402 while the other nostril is exposed to clear aroma-free atmospheric air. The device 400 may be formed and provided as an integrated device or may, as indicated in FIG. 10A, be configured to allow the active section 402 to be inserted into retainer 420 and removed when testing is completed, thereby enabling another active section 402 with another aroma and/or a different concentration therein to be inserted into retainer 420.

Figure 11A:
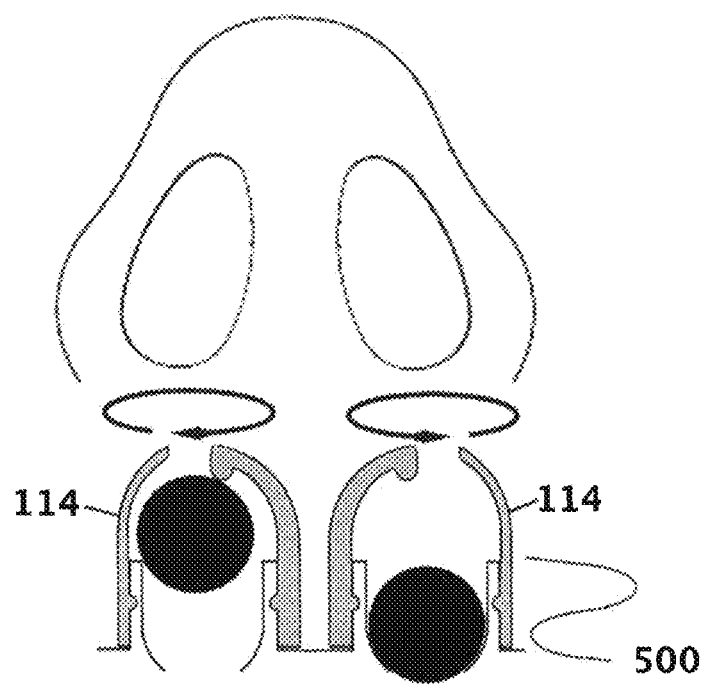
FIG. 11A illustrates a cross-sectional and cutaway view of one embodiment of a tip of the present invention.
Figure 11B:
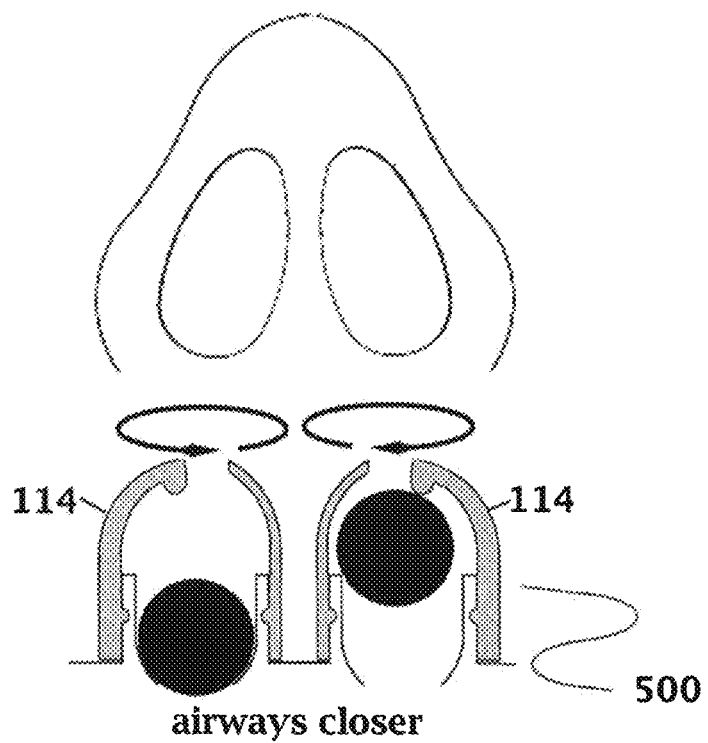
FIG. 11B illustrates a cross-sectional and cutaway view of one embodiment of the tip of FIG. 11A.

Referring now to FIGS. 11A and 11B, the device 400 may comprise a nasal tip adjustment mechanism 500 comprising a nasal tip 114 that rotates about a vertical axis, wherein the nasal aperture positions may be moved inward or outward by rotating the nasal tip 114 as shown to accommodate anatomical differences between patients, specifically the varying distances between the right and left nostrils.

In all embodiments, and specifically in the case of pure odorant-based testing, the rise/fall metric using the check ball movement 112 may be used to determine, either alone or in combination with elapsed time, and counted manually or automatically, whether one nostril comprises a lower olfactory capability than the other nostril. Staying with the pure odorant-based example, if the left and right nostrils perform statistically similarly, considering the metric(s) employed, then subject may be ruled out for early onset of Alzheimer's disease. This technique may be used with a "pure odorant detection threshold" based test as well as a "pure odorant identification threshold" based test. Alternatively, the "pure odorant identification test" may simply involve comparing the correct number of responses left vs right.

If, on the other hand, the pure odorant-based testing results in a depressed left nostril olfactory capability, then the subject may have Alzheimer's disease.

Similarly, an odorant-based (non-pure odorant) test comprising or consisting of odorants in a screening test may make use of the rise/fall of the check ball 112 metric to count breaths, either alone or in combination with time elapsed to reach the appropriate threshold. In this odorant-based case, the threshold may comprise an "odorant detection threshold" or an "odorant identification threshold." Alternatively, the "odorant identification threshold" based odorant test may comprise or consist of comparing the correct number of responses on the left to those on the right.

The test results, in any case, may be used to determine the subject's olfactory sensitivity and, in turn, identify potential issues or conditions. In the case of Alzheimer's disease, the initial testing may indicate a slight, but statistically insignificant loss in left nostril/left olfactory bulb sensitivity compared with the right. The current testing methods and devices will enable easy and frequent follow up testing to monitor the progression, if any, of the underlying condition over time.

In addition, in cases where the patient has been diagnosed with Alzheimer's disease, the present devices and methods will enable the frequent testing of the patient to (1) monitor the disease progression over time; and/or (2) monitor the efficacy of the therapeutic regimen over time.

The monitoring of the progression of the disease and/or efficacy of treatment may be based on the initial test results of the inventions described herein and/or may be based on a developed base of data which continues to refine the conclusions and the sensitivity thereof. This will include identification of certain compounds, e.g., pure odorants, which may serve as early warning mechanisms, relative to other pure odorants. It is possible, for example, that a particular pure odorant is one, or one of a group, that are the first compounds to be missed by the test subject who may be developing Alzheimer's disease. Thus, identification of these compounds will be critical in driving the screening and/or diagnosis of Alzheimer's disease to the earliest possible pre-clinical point.

Similarly, with odorant-based testing using the devices and methods described herein, it is possible to develop a baseline result for a subject with frequent and easy follow ups to determine whether the subject's olfactory capability has, in general, worsened in any respect.

The stored aroma source "A" may comprise a specific pure odorant, or a specific odorant, dependent upon whether the test purpose is to compare the left vs right nostril olfactory sensitivity or to test for general olfactory sensitivity without regard to which nostril is performing better or worse than the other.

Stored aroma sources "A" as described herein may be in the form of a liquid held in an absorbent porous material such as a wick, stiff blotter slide or a cotton ball that is placed in the aroma chamber of the test apparatus. Alternatively, a viscous material such as peanut butter could be wiped onto a slide like element and inserted into the aroma chamber or the material supplied in a disposable portion package with removable seal top. Odorants, or pure odorants, may be used as discussed herein.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. An inhaler device for presenting an aroma to one nostril of a test subject who inhales and may exhale during the aroma presentation, the device comprising:
   a lower inhalation body defining:
   an aroma storage compartment,
   at least one inhalation port in fluid communication with the ambient atmosphere;
   an aroma source disposed within the aroma storage compartment;
   an upper cover connected with the lower inhalation body and comprising a tip operatively connected with an upper housing, the tip having a nasal aperture therethrough, wherein the tip and upper housing define a check ball compartment therein, and wherein the check ball compartment is immediately adjacent and contiguous with the aroma storage compartment;
   an aperture connecting the check ball compartment in fluid communication with the aroma source compartment; and
   a check ball disposed within the check ball compartment, wherein the check ball is configured to engage a check ball seat defined within the check ball compartment and cover the aperture connecting the check ball compartment and the aroma source compartment when the test subject exhales and to disengage from the check ball seat when the test subject inhales.

2. The inhaler device of claim 1, wherein the check ball is configured to allow air flow from the aroma storage compartment to the check ball compartment when the test subject inhales and prevent air flow from the check ball compartment to the aroma storage compartment when the test subject either stops inhaling or exhales.

3. The inhaler device of claim 2, wherein the aroma storage compartment is further defined by a bottom section of the lower inhalation body, wherein the bottom section is removable.

4. The inhaler device of claim 1, further comprising keyed indicia on an external surface of the lower inhalation body, the keyed indicia correspondent with the name of the aroma source disposed within the aroma storage compartment.

5. The inhaler device of claim 1, wherein at least one of the group consisting of the upper cover, the tip and the upper housing is at least partially transparent.

6. The inhaler device of claim 1, wherein the aroma comprises either a pure odorant or an odorant.

7. The inhaler device of claim 1, further comprising the upper cover removably attached to the lower inhalation body.

8. The inhaler device of claim 2, further comprising:
   the upper housing defining a photo detection circuit therein, the photo detection circuit comprising:
   a light source incorporated into an inner surface of the check ball compartment,
   a photo detector incorporated into the inner surface of the check ball compartment at a location across the check ball compartment from the light source, the light source aligned with the photo detector and adapted to actuate the photo detector when light from the light source is sensed by the photo detector,
   a transceiver in operative communication with the photodetector, and
   a battery in operative communication with the light source, the photo detector and transceiver, and
   a switch to actuate the photo detection circuit
   wherein when the photo detection circuit is actuated, the light source emits a beam of light that is detected by the photo detector only when the check ball is in a position that allows air flow from the aroma storage compartment to the check ball compartment.

9. The inhaler device of claim 2, further comprising:
   a first light channel defined through the upper housing into the check ball compartment;
   a second light channel defined through the upper housing into the check ball compartment, the first and second light channels aligned with each other across the check ball compartment;
   a detection collar at least partially surrounding the upper housing and comprising a photo detection circuit comprising:
   a light source incorporated into the detection collar and communicating and aligned with the first light channel,
   a photo detector incorporated into the detection collar and communicating and aligned with the second light channel, the light source aligned with the photo detector and adapted to actuate the photo detector when light from the light source is detected by the photo detector,
   a transceiver in operative communication with the photodetector and adapted to receive an indication from the photo detector each time the photo detector is actuated,
   a battery in operative communication with the light source, the photo detector and transceiver, and
   a switch to actuate the photo detection circuit,
   wherein when the photo detection circuit is actuated, the light source emits a beam of light that is detected by the photo detector only when the check ball allows air flow from the aroma storage compartment to the check ball compartment.

10. The inhaler device of claim 2, further comprising a passive section comprising a nasal aperture and lumen with a second check ball within the lumen, wherein the inhaler device is configured to be presented to both the right and left nostrils of the patient at the same time.

11. An inhaler device for presenting an aroma to one nostril of a test subject who inhales and exhales during the aroma presentation, the device comprising:
   a lower inhalation body defining:
       at least one inhalation port in fluid communication with the ambient environment; an aroma source disposed within an aroma storage compartment;
   an upper cover connected with the lower inhalation body and comprising a tip operatively connected with an upper housing, the tip comprising a nasal aperture therethrough, the tip and upper housing defining an upper compartment, wherein the upper compartment is immediately adjacent and contiguous with the aroma storage compartment;
   an aperture fluidly connecting the upper compartment defined by the tip and the upper housing with the aroma source compartment; and
   a one-way valve disposed in the aperture, wherein the one-way valve is configured to allow fluid communication of air from the at least one inhalation port through the nasal aperture when the test subject inhales and to disable fluid communication of air through the nasal aperture and the at least one inhalation port when the test subject exhales.

12. A method to count breaths of a test subject, comprising:
- providing a device according to claim 1;
- instructing the test subject to breath normally while inhaling the aroma source through the nasal aperture in the tip of the device and exhaling the inhaled aroma source until reaching at least one threshold selected from the group consisting of: a pure odorant detection threshold, a pure odorant identification threshold, an odorant detection threshold, and an odorant identification threshold;
- counting the number of times the check ball rises before reaching the at least one threshold.

13. The method of claim 12, wherein the counting is done manually.

14. The method of claim 12, wherein the counting is done automatically.

15. The method of claim 14, further comprising:
- providing an electronic detector comprising a transceiver and adapted to detect when the check ball has disengaged from the check ball seat;
- detecting electronically the number of times the the check ball is detected rising from its check ball seat before reaching the selected threshold, wherein the electronically detected number corresponds with the number of breaths taken by the subject; and
- communicating the electronically detected number to the transceiver.

16. The method of claim 15, further comprising providing a programmable computing device in operative communication with the transceiver, wherein the transceiver is adapted to transmit the received electronically detected number to the programmable computing device selected from the group consisting of a computer, a table, a smartphone, and a server.

17. The method of claim 16, wherein the electronic detector further comprises a photo detector circuit comprising:
- a light source capable of emitting a light beam that is adapted to be interrupted when the check ball is engaged with the check ball seat;
- a photo detector aligned with the emitted light beam, the photo detector in operative communication with the transceiver and adapted to detect the beam of light emitted by the light source; and
- a battery in operative communication with the electronic detector.

18. The method of claim 17, further comprising:
- communicating, from the photo detector to the transceiver, the number of times the photo detector detects the beam of light emitted by the light source for each stored aroma and nostril, wherein the recorded number corresponds with the number of breaths taken by the subject;
- transmitting, from the transceiver to a programmable computing device in operative communication therewith, wherein the programmable computing device selected from the group consisting of a computer, a table, a smartphone, and a server.

19. The inhaler device of claim 5, wherein the tip is at least partially transparent and the upper housing is non-transparent such that the check ball is hidden from view when engaged with the check ball seat, and wherein the check ball is non-transparent and comprises a color that is different from a color of the upper housing.

20. The inhaler device of claim 1, wherein the lower inhalation body, tip, and check ball are oleophobic.

\* \* \* \* \*